US012650435B2

(12) United States Patent
Kaneko

(10) Patent No.: US 12,650,435 B2
(45) Date of Patent: Jun. 9, 2026

(54) MONOCLONAL ANTIBODY AGAINST AMYLOID BETA, AND METHOD FOR MEASURING AMYLOID BETA-RELATED PEPTIDE USING SAID ANTIBODY

(71) Applicant: SHIMADZU CORPORATION, Kyoto (JP)

(72) Inventor: Naoki Kaneko, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1193 days.

(21) Appl. No.: 17/623,010

(22) PCT Filed: Apr. 7, 2020

(86) PCT No.: PCT/JP2020/015717
§ 371 (c)(1),
(2) Date: Feb. 15, 2022

(87) PCT Pub. No.: WO2021/005857
PCT Pub. Date: Jan. 14, 2021

(65) Prior Publication Data
US 2022/0268789 A1     Aug. 25, 2022

(30) Foreign Application Priority Data
Jul. 5, 2019     (JP) ................................. 2019-125843

(51) Int. Cl.
*G01N 33/68*          (2006.01)
*C07K 16/18*          (2006.01)
(52) U.S. Cl.
CPC ......... *G01N 33/6896* (2013.01); *C07K 16/18* (2013.01); *G01N 2333/4709* (2013.01); *G01N 2800/2821* (2013.01)

(58) Field of Classification Search
CPC ....... G01N 33/6896; G01N 2333/4709; G01N 2800/2821; C07K 16/18; C07K 2317/34; C12N 5/12
See application file for complete search history.

(56)     References Cited

U.S. PATENT DOCUMENTS 5,750,349 A     5/1998  Suzuki et al.
2002/0102261 A1     8/2002  Raso
(Continued)

FOREIGN PATENT DOCUMENTS

| CN | 101245105 A | 8/2008 |
| CN | 102089000 A | 6/2011 |

(Continued)

OTHER PUBLICATIONS

Verwey, Nicolaas A., et al. "Quantification of amyloid-beta 40 in cerebrospinal fluid." Journal of immunological methods 348.1-2 (2009): 57-66. (Year: 2009).*
(Continued)

*Primary Examiner* — Bao-Thuy L Nguyen
*Assistant Examiner* — Christopher Evans
(74) *Attorney, Agent, or Firm* — Sughrue Mion, PLLC

(57)     ABSTRACT

The present invention provides a novel anti-Aβ antibody capable of detecting an Aβ related peptide, a method for measuring an Aβ related peptide in a biological sample by immunochemically using the above-mentioned novel anti-Aβ antibody, and a kit. A monoclonal antibody that recognizes an Aβ related peptide, and is produced by a hybridoma deposited under the accession number NITE BP-02998 at the NITE Patent Microorganisms Depositary of the National Institute of Technology and Evaluation. An antibody-immobilized carrier that includes a carrier and the monoclonal
(Continued)

antibody defined in claim 1 bound to the carrier. A kit for measuring an Aβ related peptide, comprising the antibody-immobilized carrier.

14 Claims, 8 Drawing Sheets

Specification includes a Sequence Listing.

(56) References Cited

U.S. PATENT DOCUMENTS

| | | | |
|---|---|---|---|
| 2005/0129695 A1 | 6/2005 | Mercken et al. | |
| 2006/0127954 A1 | 6/2006 | Mercken et al. | |
| 2006/0228349 A1 | 10/2006 | Acton et al. | |
| 2016/0334420 A1 | 11/2016 | Kaneko | |
| 2017/0016910 A1 | 1/2017 | Kaneko | |
| 2017/0184573 A1 | 6/2017 | Kaneko et al. | |
| 2018/0140689 A1 | 5/2018 | Kleinschmidt et al. | |
| 2018/0238909 A1 | 8/2018 | Kaneko et al. | |

FOREIGN PATENT DOCUMENTS

| | | | |
|---|---|---|---|
| JP | 2003-506321 A | 2/2003 | |
| JP | 2005-170951 A | 6/2005 | |
| JP | 2013-35843 A | 2/2013 | |
| JP | 2014-208678 A | 11/2014 | |
| JP | 2017-20980 A | 1/2017 | |
| JP | 2018-524370 A | 8/2018 | |
| WO | 2010/005858 A1 | 1/2010 | |
| WO | 2010/034072 A1 | 4/2010 | |
| WO | 2013/009703 A8 | 1/2013 | |
| WO | 2015/111430 A1 | 7/2015 | |
| WO | 2015/178398 A1 | 11/2015 | |
| WO | 2017/047529 A1 | 3/2017 | |

OTHER PUBLICATIONS

Chinese Office Action issued Dec. 28, 2023 in Application No. 202080047046.2.

Extended European Search Report dated Jun. 28, 2023 in Application No. 20837581.6.

Guriqbal S. Basi et al., "Structural Correlates of Antibodies Associated with Acute Reversal of Amyloid β-related Behavioral Deficits in a Mouse Model of Alzheimer Disease", Journal of Biological Chemistry, Jan. 29, 2010, vol. 285, No. 5, pp. 3417-3427 (11 total pages).

Luke A. Miles et al., "Amyloid-β-Anti-Amyloid-β Complex Structure Reveals an Extended Conformation in the Immunodominant B-Cell Epitope", Journal of Molecular Biology, Jan. 2008, vol. 377, pp. 181-192 (12 total pages).

Steven S. Plotkin et al., "Passive immunotherapies targeting Aβ and tau in Alzheimer's disease", Neurobiology of Disease, Jul. 16, 2020, vol. 144, pp. 1-26 (26 total pages).

Weiming Xia, PhD. et al., "A Specific Enzyme-Linked Immunosorbent Assay for Measuring β-Amyloid Protein Oligomers in Human Plasma and Brain Tissue of Patients With Alzheimer Disease", Archive of Neurology, Feb. 2009, vol. 66, No. 2, pp. 190-199 (10 total pages).

Raluca Ştefănescu et al., "Molecular characterization of the β-amyloid(4-10) epitope of plaque specific Aβ antibodies by affinity-mass spectrometry using alanine site mutation", Journal of Peptide Science, 2018, vol. 24, pp. 1-6 (6 total pages).

Naoki Kaneko et al., "Novel plasma biomarker surrogating cerebral amyloid deposition", Proc. Jpn. Acad., Ser., 2014, vol. 90, No. 9, pp. 353-364 (12 pages total).

Akinori Nakamura et al., "High performance plasma amyloid-β biomarkers for Alzheimer's disease" Nature, 2018, vol. 000 (44 pages total).

"β-Amyloid 1-16, or App (6E10)", Antibody, AlzForum, Retrieved online on Feb. 2022, Retrieved from :URL: <https://www.alzforum.org/antibodies/v-amyloid-1-16-or-app-6e10-0> (2 pages total).

K.S. Kim et al., "Detection and Quantitation of Amyloid B-Peptide With 2 Monoclonal Antibodies", Neuroscience Research Communications, 1990, vol. 7, No. 2, pp. 113-122 (10 pages total).

Muthu Ramakrishnan et al., "Surface Plasmon Resonance Binding Kinetics of Alzheimer's Disease Amyloid β Peptide Capturing- and Plaque Binding-Monoclonal Antibodies†", Biochemistry, 2009, vol. 48, No. 43, pp. 1-20 (20 pages total).

Rong Wang et al., "The Profile of Soluble Amyloid B Protein in Cultured Cell Media", The Journal of Biological Chemistry, 1996, vol. 271, No. 50, pp. 31894-31902 (10 pages total).

"Harvest Mouse And Technomouse—Towards production of monoclonal antibody in vitro" ASAS, 1995, Retrieved from: URL: <http://www.asas.or.jp/jsaae/jsaae/news/3.html> (16 pages total).

International Preliminary Report on Patentability dated Jan. 11, 2022 in International Application No. PCT/JP2020/015717.

Office Action dated Jan. 6, 2023 issued by the Japanese Patent Office in Japanese Application No. 2021-530493.

Communication dated Jul. 22, 2024 from The State Intellectual Property Office of the P.R. of China in Application No. 202080047046.2.

\* cited by examiner

Fig.1

Formation Path of Aβ Peptides from APP

Fig.6

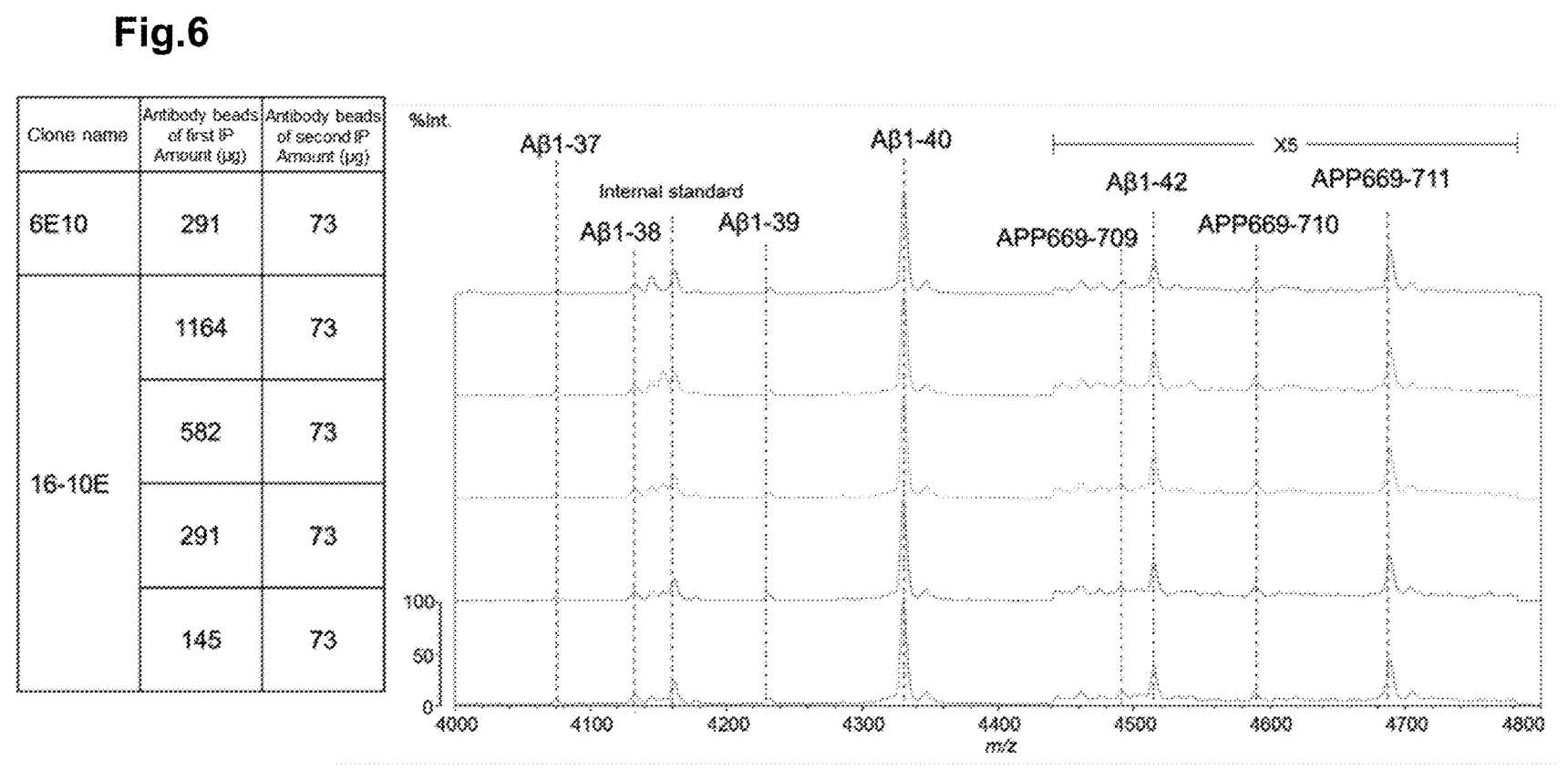

| Clone name | Antibody beads of first IP Amount (μg) | Antibody beads of second IP Amount (μg) |
|---|---|---|
| 6E10 | 291 | 73 |
| 16-10E | 1164 | 73 |
| | 582 | 73 |
| | 291 | 73 |
| | 145 | 73 |

MONOCLONAL ANTIBODY AGAINST AMYLOID BETA, AND METHOD FOR MEASURING AMYLOID BETA-RELATED PEPTIDE USING SAID ANTIBODY

CROSS REFERENCE TO RELATED APPLICATIONS

This application is a National Stage of International Application No. PCT/JP2020/015717 filed on Apr. 7, 2020, claiming priority based on Japanese Patent Application No. 2019-125843 filed on Jul. 5, 2019.

TECHNICAL FIELD

The present invention relates to a monoclonal antibody against amyloid beta, and method for measuring amyloid beta-related peptide using said antibody.

BACKGROUND ART

Alzheimer's disease (AD) is a principal cause of dementia, and occupies 50 to 60% of the entire dementia. The number of patients suffering from dementia was more than or equal to 24 million in the world in 2001, and is estimated to reach 82 million in 2030. It is considered that an $A\beta$ is deeply involved in development of Alzheimer's disease. The amyloid $\beta$ ($A\beta$) is produced as a result of proteolysis of amyloid precursor protein (APP) which is a single-pass transmembrane protein composed of 770 amino acid residues, by $\beta$ secretase and $\gamma$ secretase (refer to FIG. 1). Appearance of senile plaques due to aggregation of $A\beta$ accompanying fibrosis triggers aggregation and accumulation of tau protein inside neurocytes to cause nerve malfunction and neuronal cell death. It is considered that this results in extreme deterioration of the cognitive ability. It has long been known that $A\beta$ mainly consists of 40 mer ($A\beta1$-40) and 42 mer ($A\beta1$-42), and migrates into cerebrospinal fluid (CSF). Furthermore, it is suggested that there is some possibility that $A\beta$ also migrates into blood. Further, in recent years, existence of $A\beta$-like peptides having lengths different from those of $A\beta1$-40 and $A\beta1$-42 in CSF has been reported.

As for $A\beta$, the present inventor et al. have reported in the recent research that the ratio of APP669-711 which is one of $A\beta$ related peptides ($A\beta$-like peptides) to $A\beta1$-42 is promising as a blood biomarker (Non-Patent Document 1, and Patent Document 1: WO 2015/178398). These $A\beta$ and $A\beta$ related peptides are quantified by an immunoprecipitation method (IP) followed by a mass spectrometry (MALDI-TOF MS).

Furthermore, the present inventor et al. have disclosed in Patent Document 2: WO 2017/047529 that a numerical value by a combination of two or more ratios selected from the group consisting of three ratios, $A\beta1$-39/$A\beta1$-42, $A\beta1$-40/$A\beta1$-42, and APP669-711/$A\beta1$-42, regarding $A\beta$ and $A\beta$ related peptides ($A\beta$-like peptides), through a mathematical technique is promising as a blood biomarker. These $A\beta$ and $A\beta$ related peptides are quantified by an immunoprecipitation method (IP) followed by a mass spectrometry (MALDI-TOF MS).

As mentioned above, the present inventor et al. have discovered by using a mass spectrometry (MALDI-TOF MS) that a ratio between APP669-711 which is one of $A\beta$ related peptides and $A\beta1$-42 is promising as a candidate for a blood biomarker. Furthermore, the present inventor et al. have reported that a composite biomarker by a combination of the ratio of APP669-711/$A\beta1$-42 and the ratio of $A\beta1$-40/$A\beta1$-42 can estimate a cerebral amyloid accumulation with high accuracy through the use of multiple specimens in Japan and Australia, accordingly, the composite biomarker is a reliable and versatile biomarker (Non-Patent Document 2).

A mass spectrometry (MALDI-TOF MS) is useful as an analysis technique for biomarkers such as $A\beta$ related peptides including APP669-711. Meanwhile, as the other analysis technique, a sandwich ELISA is a widely and generally used measurement method as a clinical examination method and is a low cost method. Accordingly, the sandwich ELISA can be a useful analysis technique.

At present, an ELISA Kit capable of analyzing $A\beta1$-40 and $A\beta1$-42 in the plasma is commercially available from respective makers (Wako Pure Chemical Corporation, IBL, etc.).

Patent Document 3: JP-A-2005-170951 discloses the monoclonal antibodies BAN-52a and BAN-50a that recognize the N-terminal portion of an amyloid $\beta$ ($A\beta1$-16), and the monoclonal antibodies BA-27a, BS-85 and BC-05a that specifically recognize the C-terminal portion of an amyloid $\beta$, and discloses a sandwich EIA which is specific to $A\beta1$-40 and $A\beta1$-42.

Patent Document 4: JP-A-2014-208678 discloses an antibody that specifically recognizes $A\beta11$-x, and discloses a sandwich ELISA to $A\beta11$-40 and a western blotting to $A\beta11$-x.

So far, in an Immunoprecipitation-Mass spectrometry (IP-MS) for a blood biomarker ($A\beta$ and $A\beta$ related peptides), an Immunoprecipitation (IP) using anti-$A\beta$ antibody clone 6E10 has been carried out (Non-Patent Documents 1, 2 and 3, and Patent Documents 5, 6, 7 and 8). The clone 6E10 has a strong affinity to $A\beta$, and has been used for an immunoassay method and an IP-MS by many researchers since early times (Non-Patent Documents 4, 5 and 6). Actually, 6E10 gave the data indicating that $A\beta$ related peptides can be detected with the highest sensitivity by using 6E10 even if compared with the data of IP-MS by using the other commercially available clones, and therefore, it can be said that 6E10 is an excellent antibody clone. The 6E10 is obtained by transplanting hybridoma cells into an abdominal cavity of a mouse to produce an antibody in ascitic fluid. And then, the produced antibody is purified using Protein G, and the resulting purified product is bound onto magnetic beads to prepare antibody-immobilized beads. The antibody-immobilized beads are used in IP.

Patent Document 5: WO 2015/111430 (Patent Document 6: US 2016/0334420) discloses a measurement method for APP cleavage peptides.

Patent Document 7: JP-A-2017-20980 (Patent Document 8: US 2017/0016910) discloses a mass spectrometry method for polypeptides.

PRIOR ART DOCUMENTS

Patent Documents

Patent Document 1: WO 2015/178398
Patent Document 2: WO 2017/047529
Patent Document 3: JP-A-2005-170951
Patent Document 4: JP-A-2014-208678
Patent Document 5: WO 2015/111430
Patent Document 6: US 2016/0334420
Patent Document 7: JP-A-2017-20980
Patent Document 8: US 2017/0016910

Non-Patent Documents

Non-Patent Document 1: Kaneko N, Nakamura A, Washimi Y, Kato T, Sakurai T, Arahata Y, Bundo M, Takeda A, Niida S, Ito K, Toba K, Tanaka K, Yanagisawa K.: Novel plasma biomarker surrogating cerebral amyloid deposition. Proc Jpn Acad Ser B Phys Biol Sci. 2014; 90(9): 353-364.

Non-Patent Document 2: Nakamura A, Kaneko N, Villemagne V L, Kato T, Doecke J, Dore V, Fowler C, Li Q X, Martins R, Rowe C, Tomita T, Matsuzaki K, Ishii K, Ishii K, Arahata Y, Iwamoto S, Ito K, Tanaka K, Masters C L, Yanagisawa K.: High performance plasma amyloid-β biomarkers for Alzheimer's disease. Nature. 2018; 554 (7691): 249-254.

Non-Patent Document 3: In regard to 6E10: https://www.alzforum.org/antibodies/v-amyloid-1-16-or-app-6 e10-0

Non-Patent Document 4: Kim K S, Wen G Y, Bancher C, Chen C M, Sapienza V J, Hong H, Wisniewski H M.: Detection and quantitation of amyloid b-peptide with 2 monoclonal antibodies. Neurosci Res Commun. 1990; 7(2): 113-122.

Non-Patent Document 5: Ramakrishnan M, Kandimalla K K, Wengenack T M, Howell KG, Poduslo J F.: Surface plasmon resonance binding kinetics of Alzheimer's disease amyloid beta peptide-capturing and plaque-binding monoclonal antibodies. Biochemistry. 2009; 48(43): 10405-15.

Non-Patent Document 6: Wang R, Sweeney D, Gandy S E, Sisodia SS: The profile of soluble amyloid beta protein in cultured cell media. Detection and quantification of amyloid beta protein and variants by immunoprecipitation-mass spectrometry. J Biol Chem. 1996; 13; 271(50): 31894-902.

Non-Patent Document 7: In regard to an ascitic fluid method: http://www.asas.or.jp/jsaae_old/news/3.html; (Item: "Harvest Mouse And Technomouse—Towards production of monoclonal antibody in vitro—".

Non-Patent Document 8: In regard to an ascitic fluid method: http://www.asas.or.jp/jsaae_old/news/3.html: (Item: column of Antibody Shape—Ascites Fluid)

SUMMARY OF THE INVENTION

Problems to be Solved by the Invention

Other anti-Aβ antibody is not known that can detect an Aβ related peptide with a high sensitivity as with 6E10.

And, regarding the production of monoclonal antibody by an ascitic fluid method, like production of 6E10, it generally becomes difficult to conduct the production of monoclonal antibody by an ascitic fluid method from an animal ethical point of view (Non-Patent Document 7). Furthermore, there is a possibility that IgG derived from the host is mixed by an ascitic fluid method (Non-Patent Document 8).

From these circumstances, it is desired that a novel anti-Aβ antibody as an alternative to 6E10 is produced, said novel anti-Aβ antibody being capable of detecting an Aβ related peptide with a high sensitivity as with 6E10. Furthermore, it is also desired that a novel anti-Aβ antibody as an alternative to 6E10 is obtained not only by an ascitic fluid method but even also from a culture supernatant.

Therefore, an object of the present invention is to provide a novel anti-Aβ antibody capable of detecting an Aβ related peptide. And, an object of the present invention is also to provide a novel anti-Aβ antibody capable of detecting an Aβ related peptide, said novel anti-Aβ antibody being produced not only by an ascitic fluid method but even also from a culture supernatant.

Furthermore, an object of the present invention is to provide a method for measuring an Aβ related peptide in a biological sample by immunochemically using the above-mentioned novel anti-Aβ antibody. That is, an object of the present invention is to provide a method for measuring an Aβ related peptide by an Immunoprecipitation (IP), a method for measuring an Aβ related peptide by an Immunoprecipitation-Mass spectrometry (IP-MS), and a method for measuring an Aβ related peptide by a continuous Immunoprecipitation-Mass spectrometry (cIP-MS), each method using the novel anti-Aβ antibody capable of detecting an Aβ related peptide.

Furthermore, an object of the present invention is to provide a kit for measuring an Aβ related peptide, said kit comprising an antibody-immobilized carrier including the above-mentioned novel anti-Aβ antibody.

Furthermore, an object of the present invention is to provide a novel anti-Aβ antibody that can recognize Aβ3-8 peptide (SEQ ID NO: 1).

Means for Solving the Problems

As a result of diligent efforts, the present inventor, in order to produce an antibody that recognizes an Aβ related peptide, has immunized a KLH conjugated synthetic peptide DAEFRHDSGYEVHHQKC (SEQ ID NO: 10; this sequence is equivalent to a sequence wherein Cys (C) is conjugated to Lys (K) at C terminal of Aβ1-16) to mice, and conducted cell fusion and ELISA screening, and thereby has obtained 6 clones of each hybridoma that produces an antibody recognizing the Aβ related peptide. The antibodies of 6 clones were used to evaluated by IP-MS, and the present inventor has obtained a novel antibody of one clone capable of detecting the Aβ related peptide in blood plasma by IP-MS. The present inventor has also constructed a kit for measuring an Aβ related peptide in blood plasma by IP-MS, said kit comprising the above novel anti-Aβ antibody as a constituent component.

The present invention includes the following aspects.

A first aspect of the present invention is: a monoclonal antibody that recognizes an Aβ related peptide, and is produced by a hybridoma deposited under the accession number NITE BP-02998 at the NITE Patent Microorganisms Depositary of the National Institute of Technology and Evaluation; and a hybridoma deposited under the accession number NITE BP-02998 at the NITE Patent Microorganisms Depositary of the National Institute of Technology and Evaluation.

A second aspect of the present invention is a method for measuring an Aβ related peptide in a biological sample, the method comprising:

a reaction step of bringing a liquid containing a biological sample into contact with an antibody-immobilized carrier that includes a carrier and the above-mentioned monoclonal antibody bound to the carrier, to bind an Aβ related peptide in the biological sample with the antibody-immobilized carrier;

a washing step of washing the antibody-immobilized carrier to which the Aβ related peptide is bound;

an eluting step of dissociating and eluting the Aβ related peptide from the antibody-immobilized carrier by using an acidic solution to obtain a purified solution; and a step of detecting the Aβ related peptide in the purified solution by mass spectrometry.

A third aspect of the present invention is a method for measuring an Aβ related peptide in a biological sample, the method comprising:

a first reaction step of bringing a liquid containing a biological sample into contact with a first antibody-immobilized carrier that includes a carrier and the above-mentioned monoclonal antibody bound to the carrier, to bind an Aβ related peptide in the biological sample with the first antibody-immobilized carrier;

a first washing step of washing the first antibody-immobilized carrier to which the Aβ related peptide is bound;

a first eluting step of dissociating and eluting the Aβ related peptide from the first antibody-immobilized carrier by using an acidic solution to obtain a first eluate, a neutralizing step of making pH of the eluate neutral by adding a neutral buffer to the first eluate to obtain a first purified solution with neutralized pH;

a second reaction step of bringing the first purified solution into contact with a second antibody-immobilized carrier that includes a carrier and the above antibody bound to the carrier, to bind the Aβ related peptide in the first purified solution with the second antibody-immobilized carrier;

a second washing step of washing the second antibody-immobilized carrier to which the Aβ related peptide is bound;

a second eluting step of dissociating and eluting the Aβ related peptide from the second antibody-immobilized carrier by using an acidic solution to obtain a second purified solution; and a step of detecting the Aβ related peptide in the second purified solution by mass spectrometry.

A fourth aspect of the present invention is a method for measuring an Aβ related peptide in a biological sample, the method comprising:

a reaction step of bringing a liquid containing a biological sample into contact with the above-mentioned monoclonal antibody, to bind an Aβ related peptide in the biological sample with the monoclonal antibody;

a step of detecting the Aβ related peptide binding with the monoclonal antibody by a method selected from the group consisting of a sandwich immunoassay method, a direct ELISA, an indirect ELISA, a competitive ELISA, a western blotting, an immunohistochemistry, a flow cytometry, an immunoprecipitation, an affinity chromatography, and an immunocytochemistry.

A fifth aspect of the present invention is: a monoclonal antibody that recognizes Aβ3-8 peptide; and a monoclonal antibody that recognizes Aβ3-8 peptide, and is produced by a hybridoma deposited under the accession number NITE BP-02998 at the NITE Patent Microorganisms Depositary of the National Institute of Technology and Evaluation.

Effects of the Invention

The present invention provides a hybridoma cell clone 16-10E deposited under the accession number NITE BP-02998; and provides a novel anti-Aβ antibody that recognizes an Aβ related peptide, and is produced from the hybridoma cell clone 16-10E.

The present invention provides a method for measuring an Aβ related peptide in a biological sample by immunochemically using the above novel anti-Aβ antibody clone 16-10E, that is, a method for measuring an Aβ related peptide by an Immunoprecipitation (IP), a method for measuring an Aβ related peptide by an Immunoprecipitation-Mass spectrometry (IP-MS), and a method for measuring an Aβ related peptide by a continuous Immunoprecipitation-Mass spectrometry (cIP-MS).

Furthermore, the present invention provides a kit for measuring an Aβ related peptide, said kit comprising an antibody-immobilized carrier including the anti-Aβ antibody clone 16-10E.

Furthermore, the present invention provides a novel monoclonal antibody that recognizes Aβ3-8 peptide (SEQ ID NO: 1).

BRIEF DESCRIPTION OF DRAWINGS

FIG. 1 is a diagram schematically showing the generation route of Aβ peptides by proteolysis of amyloid precursor protein (APP).

FIG. 6 shows IP-MS spectra by changing amount of the 16-10E antibody-immobilized beads in the first IP. The horizontal axis indicates m/z, and the vertical axis indicates relative intensity of ion. Each IP-MS spectrum shows the results as to the anti-Aβ antibody clone 6E10 (control, beads amount in the first IP: 291 μg) , and the anti-Aβ antibody clone 16-10E (beads amount in the first IP: 1164, 582, 291, or 145) in order from the top. The antibody beads amounts used are as indicated at the Table in the FIG. 6, and are indicated as beads weight, in Example 3-1.

MODES FOR CARRYING OUT THE INVENTION

Figure 2:
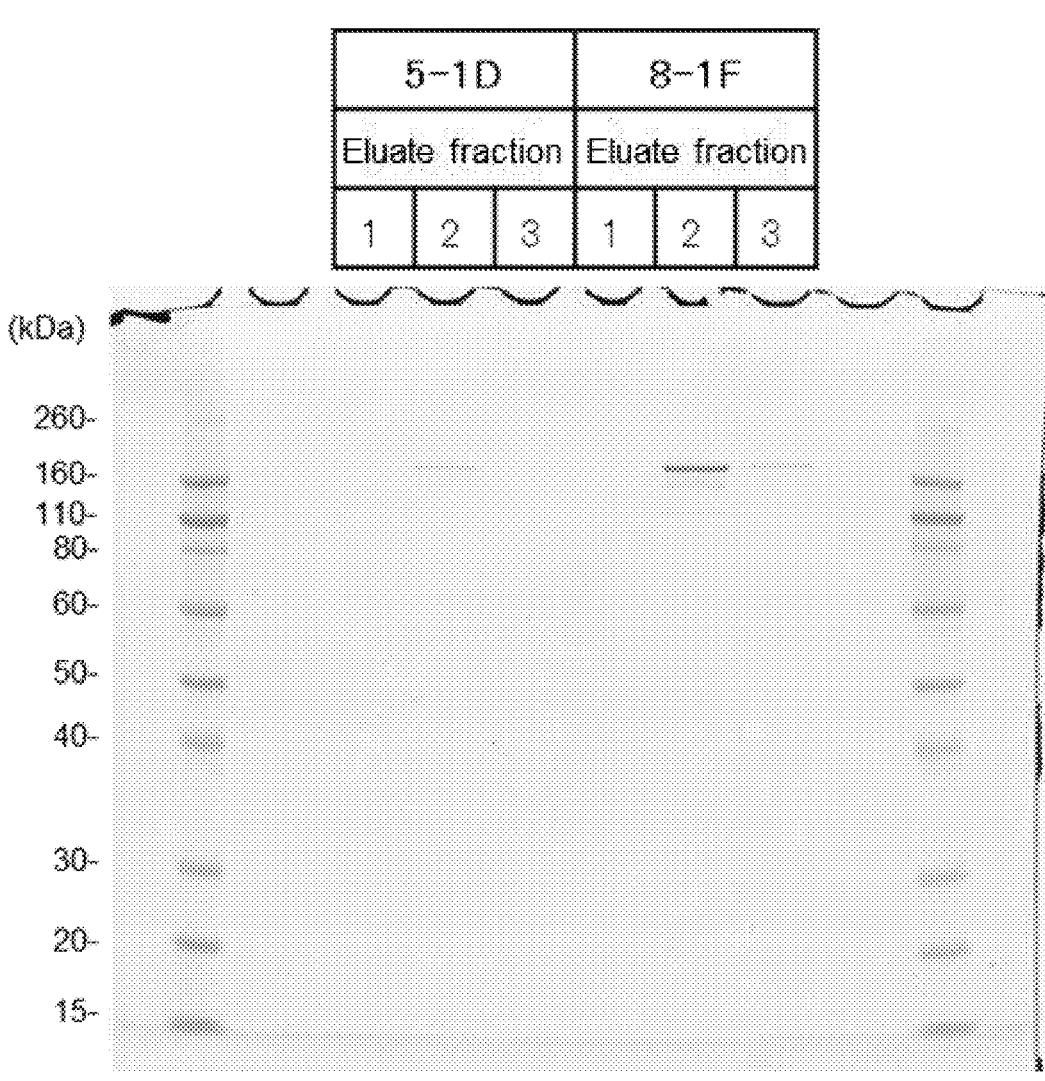
FIG. 2 shows the results of confirmation by SDS-PAGE after purifying the culture supernatant of the hybridoma (clone 5-1D, 8-1F) by the ammonium sulfate precipitation and Protein G, in Example 1.

1. Monoclonal Antibody Recognizing Aβ Related Peptide

In the present invention, a monoclonal antibody that recognizes an Aβ related peptide is produced by a hybridoma (clone 16-10E) deposited under the accession number NITE BP-02998 at the NITE Patent Microorganisms Depositary (NPMD) of the National Institute of Technology and Evaluation (NITE).

Deposit of Biological Material

Hybridoma 16-10E, which produces the monoclonal antibody described herein, was deposited with the National Institute of Technology and Evaluation (NITE), an International Depositary Authority under the Budapest Treaty, located at 2-5-8 Kazusakamatari, Kisarazu-shi, Chiba 292-0818, Japan. The deposit was made on Jun. 27, 2019 and has been assigned Accession No. NITE BP-02998. The deposit was made under the terms of the Budapest Treaty on the International Recognition of the Deposit of Microorganisms for the Purposes of Patent Procedure. The deposited material will be made available to the public upon grant of a patent, and the deposit will be replaced if it becomes non-viable.

The above hybridoma (clone 16-10E) deposited under the accession number NITE BP-02998 has an ability to produce a monoclonal antibody that recognizes an Aβ related peptide.

In order to produce a monoclonal antibody of the present invention that recognizes an Aβ related peptide, the present inventor has immunized a KLH (Keyhole Limpet Hemocyanin) conjugated synthetic peptide DAEFRHDSGYEVHHQKC (SEQ ID NO: 10) to mice, and conducted cell fusion and screening, and thereby has obtained a hybridoma (clone 16-10E) that produces a monoclonal antibody recognizing the Aβ related peptide. More detailed production of the antibody is described in the Examples. As described in the Examples, the monoclonal antibody of the present invention that recognizes an Aβ related peptide can be obtained not by an ascitic fluid method but even also from a culture supernatant of cell fusion.

The above sequence DAEFRHDSGYEVHHQKC (SEQ ID NO: 10) is equivalent to a sequence wherein Cys (C) is conjugated to Lys (K) at C terminal of 41-16.

Further, the monoclonal antibody of the present invention that recognizes an Aβ related peptide is a monoclonal antibody that also recognizes Aβ3-8 peptide EFRHDS (SEQ ID NO: 1) itself.

The known clone 6E10 is used as an antibody that recognizes an Aβ related peptide with an epitope of Aβ3-8, however, the clone 6E10 has no reactivity with Aβ3-8 peptide itself as indicated in the item of the Examples. These results show that the anti-Aβ antibody clone 16-10E of the present invention and the clone 6E10 have different reactivities with Aβ3-8 peptide EFRHDS (SEQ ID NO: 1) to each other. Accordingly, the monoclonal antibody of the present invention that recognizes an Aβ related peptide is a novel antibody.

Aβ Related Peptide

Figure 1:
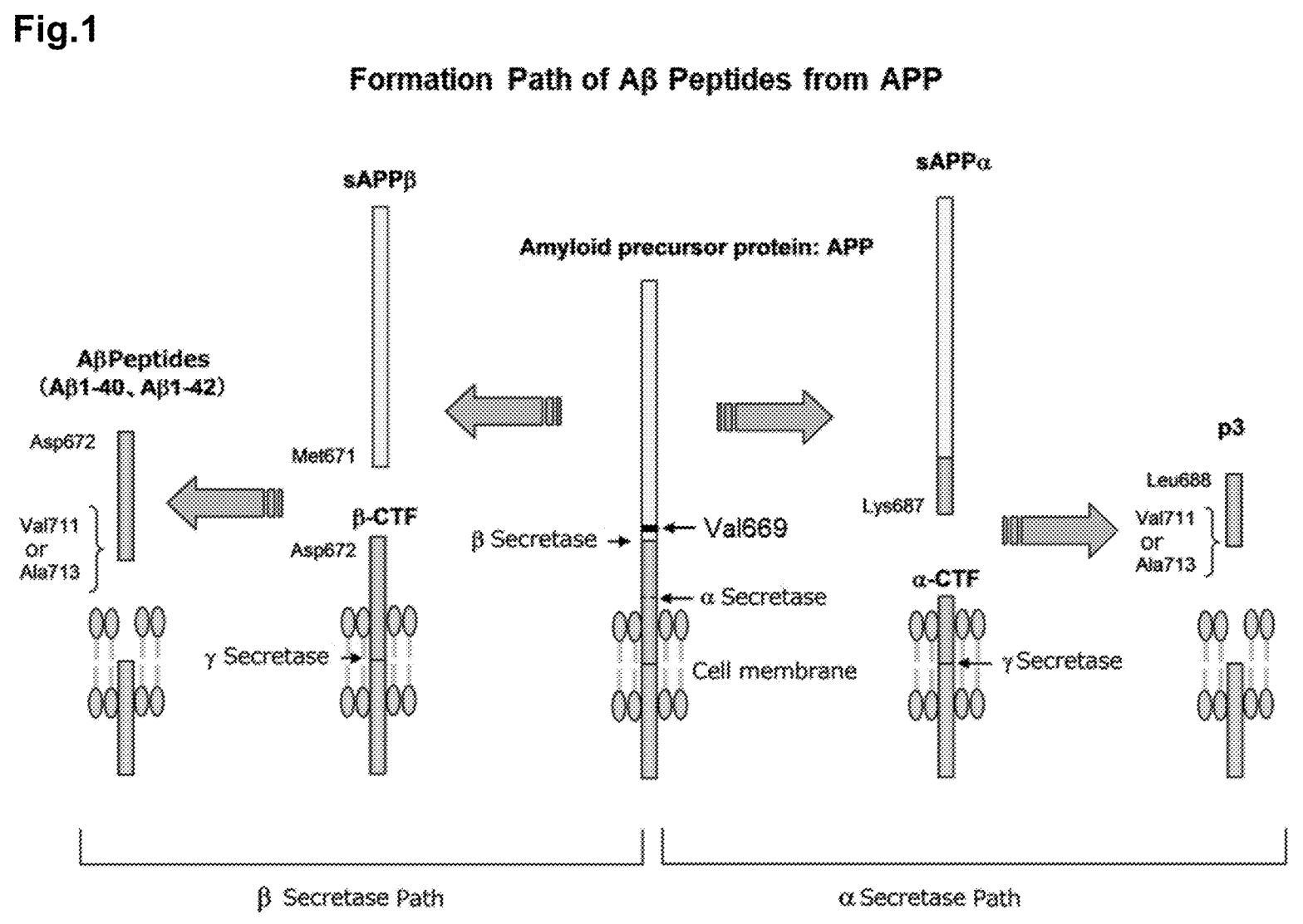

An Aβ related peptide is produced as a result of proteolysis of amyloid precursor protein (APP) which is composed of full-length 770 amino acid residues by a protease including β secretase, γ secretase and the like, and the Aβ related peptide includes various molecular species (refer to FIG. 1). As mentioned above, the anti-Aβ antibody clone 16-10E of the present invention recognizes Aβ3-8 peptide EFRHDS (SEQ ID NO: 1). Therefore, in the present invention, an Aβ related peptide that is recognized by the above anti-Aβ antibody, preferably means to include at least the peptide sequence EFRHDS (SEQ ID NO: 1) of the third to the eighth of Aβ.

Examples of the Aβ related peptides include, but not limited to, following peptides: APP663-711, APP664-711, APP666-709, APP666-711, APP669-709 (SEQ ID NO: 7), APP669-710 (SEQ ID NO: 8), APP669-711 (SEQ ID NO: 9), APP669-713, APP671-711, APP672-708 (SEQ ID NO: 2), APP672-709 (SEQ ID NO: 3), APP672-710 (SEQ ID NO: 4), APP672-711 (SEQ ID NO: 5), APP672-713 (SEQ ID NO: 6), APP674-711, and APP674-679 (SEQ ID NO: 1).

```
APP674-679 (Aβ3-8) (SEQ ID NO: 1):
EFRHDS

APP672-708 (Aβ1-37) (SEQ ID NO: 2):
DAEFRHDSGYEVHHQKLVFFAEDVGSNKGAIIGLMVG

APP672-709 (Aβ1-38) (SEQ ID NO: 3):
DAEFRHDSGYEVHHQKLVFFAEDVGSNKGAIIGLMVGG

APP672-710 (Aβ1-39) (SEQ ID NO: 4):
DAEFRHDSGYEVHHQKLVFFAEDVGSNKGAIIGLMVGGV

APP672-711 (Aβ1-40) (SEQ ID NO: 5):
DAEFRHDSGYEVHHQKLVFFAEDVGSNKGAIIGLMVGGVV

APP672-713 (Aβ1-42) (SEQ ID NO: 6):
DAEFRHDSGYEVHHQKLVFFAEDVGSNKGAIIGLMVGGVVIA

APP669-709 (Aβ(-3-38)) (SEQ ID NO: 7):
VKMDAEFRHDSGYEVHHQKLVFFAEDVGSNKGAIIGLMVGG

APP669-710 (Aβ(-3-39)) (SEQ ID NO: 8):
VKMDAEFRHDSGYEVHHQKLVFFAEDVGSNKGAIIGLMVGGV

APP669-711 (Aβ(-3-40)) (SEQ ID NO: 9):
VKMDAEFRHDSGYEVHHQKLVFFAEDVGSNKGAIIGLMVGGVV
```

As described above, APP674-679 and Aβ3-8 indicate the same peptide. And, similarly, APP672-709 and Aβ1-38 indicate the same peptide, APP672-711 and Aβ1-40 indicate the same peptide, APP672-713 and Aβ1-42 indicate the same peptide, APP669-709 and Aβ(-3-38) indicate the same peptide, APP669-710 and Aβ(-3-39) indicate the same peptide, and APP669-711 and Aβ(-3-40) indicate the same peptide. The same applies to other peptides.

Antibody-Immobilized Carrier

An antibody-immobilized carrier of the present invention comprises a carrier, and the above monoclonal antibody of the present invention that recognizes an Aβ related peptide and is bound to the carrier.

The material of the carrier used herein may be a known material, and for example, may be selected from the group consisting of agarose, sepharose, dextran, silica gel, polyacrylamide, polystyrene, polyethylene, polypropylene, polyester, polyacrylonitrile, (meth)acrylic acid polymer, fluororesin, metal complex resin, glass, metal, and a magnetic substance.

The carrier may have any shape including a planar shape, a globular shape and other shapes. For example, the carrier may be a chip, or beads or may form a flow channel wall inside a micro device used for separation and/or concentration of a target substance. The carrier surface has a bonding functional group.

The antibody may be bound to the carrier via a spacer. As the spacer, those known in the art can be used, and an example thereof includes a high molecular weight polymer.

Examples of the high molecular weight polymer include an alkylene group and an oxyalkylene group.

For example, the spacer may be an organic high molecular weight polymer selected from the group consisting of poly-oxyalkylated polyol, polyvinyl alcohol, polyvinyl alkyl ether, polysaccharide, biodegradable polymer, and lipid polymer. The alkyl group in the polyoxyalkylated polyol and the polyvinyl alkyl ether may be, for example, a C1 to C6 alkyl group, preferably a C1 to C3 alkyl group. Examples of the polysaccharide include dextran, mucopolysaccharide, and chitins. An example of the mucopolysaccharide includes hyaluronic acid. Examples of the biodegradable polymer include PLA (poly (lactic acid)) and PLGA (poly(lactic-glycolic acid)).

The spacer may be those containing one kind of the above examples, or may be those containing two or more kinds arbitrarily selected from the above examples. The spacer may be linear or branched.

The antibody-immobilized carrier used in the present invention can be prepared by binding a carrier, and an antibody, and a spacer substance if used, via respective bonding functional groups such as a covalently bonding functional group, an ionic-bonding functional group, and a hydrogen bonding functional group possessed by these elements by a known method depending on the kinds of the functional groups. In the embodiments of the present invention, in the case of measuring an Aβ related peptide by a continuous Immunoprecipitation-Mass spectrometry (cIP-MS), the first antibody-immobilized carrier and the second antibody-immobilized carrier may be the same or different from each other.

Measurement Method of Aβ Related Peptide (Measurement Method of Aβ Related Peptide by Immuno-precipitation-Mass Spectrometry (IP-MS))

A second aspect of the present invention is a method for measuring an Aβ related peptide in a biological sample, the method comprising:

a reaction step of bringing a liquid containing a biological sample into contact with an antibody-immobilized carrier that includes a carrier and the above-mentioned monoclonal antibody bound to the carrier, to bind an Aβ related peptide in the biological sample with the antibody-immobilized carrier;

a washing step of washing the antibody-immobilized carrier to which the Aβ related peptide is bound;

an eluting step of dissociating and eluting the Aβ related peptide from the antibody-immobilized carrier by using an acidic solution to obtain a purified solution; and a step of detecting the Aβ related peptide in the purified solution by mass spectrometry.

(Measurement Method of Aβ Related Peptide by Continuous Immunoprecipitation-Mass Spectrometry (cIP-MS))

Furthermore, a third aspect of the present invention is a method for measuring an Aβ related peptide in a biological sample, the method comprising:

a first reaction step of bringing a liquid containing a biological sample into contact with a first antibody-immobilized carrier that includes a carrier and the above-mentioned monoclonal antibody bound to the carrier, to bind an Aβ related peptide in the biological sample with the first antibody-immobilized carrier;

a first washing step of washing the first antibody-immo-bilized carrier to which the Aβ related peptide is bound;

a first eluting step of dissociating and eluting the Aβ related peptide from the first antibody-immobilized carrier by using an acidic solution to obtain a first eluate, a neutralizing step of making pH of the eluate neutral by adding a neutral buffer to the first eluate to obtain a first purified solution with neutralized pH;

a second reaction step of bringing the first purified solution into contact with a second antibody-immobilized carrier that includes a carrier and the above antibody bound to the carrier, to bind the Aβ related peptide in the first purified solution with the second antibody-immobilized carrier;

a second washing step of washing the second antibody-immobilized carrier to which the Aβ related peptide is bound;

a second eluting step of dissociating and eluting the Aβ related peptide from the second antibody-immobilized carrier by using an acidic solution to obtain a second purified solution; and a step of detecting the Aβ related peptide in the second purified solution by mass spectrometry.

Thus, in the continuous Immunoprecipitation-Mass spectrometry (cIP-MS), after the neutralizing step, a binding reaction step, a washing step, and a dissociating and eluting step are repeated. A detailed explanation is described below for the continuous Immunoprecipitation-Mass spectrometry (cIP-MS), and the detailed explanation also includes an explanation for Immunoprecipitation-Mass spectrometry (IP-MS). That is, in case of conducting Immunoprecipitation-Mass spectrometry (IP-MS), a first eluate of a first eluting step may be subjected to mass spectrometry.

(First Binding Reaction Step)

First, a liquid containing a biological sample (normally, containing a biological sample and a binding solution) is brought into contact with the first antibody-immobilized carrier, to bind the first antibody-immobilized carrier with a target Aβ related peptide contained in the biological sample.

The biological sample includes body fluids such as blood, cerebrospinal fluid (CSF), urine, body secretory fluid, saliva, and sputum; and feces. The blood sample includes whole blood, plasma, serum and the like. The blood sample can be prepared by appropriately treating whole blood collected from an individual. The treatment conducted in the case of preparing a blood sample from collected whole blood is not particularly limited, and any treatment that is clinically acceptable may be conducted. For example, centrifugal separation or the like may be conducted. The blood sample subjected to the binding step may be appropriately stored at low temperature by freezing in the intermediate stage of the preparation step or in the post stage of the preparation step. In the present invention, the biological sample is disposed of rather than being returned to the individual from which the blood sample is derived. The use of a blood sample as a subject sample is preferable in that collection of a sample is minimally invasive when the sample is solid or cerebrospinal fluid, and that a blood sample is a subject sample for screening of various diseases in a general medical examination, a thorough physical examination and the like.

As the binding solution, a binding solution that is used in ordinary immunoprecipitation (IP) can be used. The composition of the binding solution preferably includes a surfactant for suppressing non-specific adsorption. As the surfactant, preferred is a neutral surfactant that is less likely to cause denaturation of protein such as antibody, is easily removed in the washing step, and does not suppress a signal of the target Aβ related peptide even if the surfactant is contaminated in the subsequent mass spectrometry. Specific examples of the surfactant include a neutral surfactant having maltose in a hydrophilic part, a neutral surfactant having trehalose in a hydrophilic part, and a neutral surfactant having glucose in a hydrophilic part. The hydrophobic part of such a neutral surfactant is, but not particularly limited to, preferably an about C7 to C14 alkyl group. The binding solution is preferably a neutral buffer containing the surfactant selected from the above-mentioned surfactants.

Examples of the neutral surfactant having maltose in a hydrophilic part include:

n-Decyl-β-D-maltoside (DM) [cmc: 0.087%]

n-Dodecyl-β-D-maltoside (DDM) [cmc: 0.009%]

n-Nonyl-β-D-thiomaltoside (NTM) [cmc: 0.116%], and the like. The "cmc" represents critical micelle concentration.

Examples of the neutral surfactant having trehalose in a hydrophilic part include:

α-D-Glucopyranosyl-α-Dglucopyranoside monooctanoate (Trehalose C8) [cmc: 0.262%]

α-D-Glucopyranosyl-α-Dglucopyranoside monododecanoate (Trehalose C12) [cmc: 0.008%]

α-D-Glucopyranosyl-α-Dglucopyranoside monomyristate (Trehalose C14) [cmc: 0.0007%], and the like.

Examples of the neutral surfactant having glucose in a hydrophilic part include:

n-Octyl-β-D-thioglucoside (OTG) [cmc: 0.278%]

n-Octyl-β-D-glucoside (OG) [cmc: 0.731%]

n-Heptyl-β-D-thioglucoside (HTG) [cmc: 0.883%], and the like.

One or a combination of two or more of the aforementioned neutral surfactants can be used. The neutral surfactant to be used is selected appropriately depending on the carrier, the antibody and the target polypeptides to be used.

The neutral buffer as the binding solution has a surfactant concentration of, for example, 0.001 to 10% (v/v), preferably 0.01 to 5% (v/v), more preferably 0.05 to 2% (v/v), although the surfactant concentration is not particularly limited. By employing such a surfactant concentration, binding reaction between the antibody and the target polypeptides to be bound is likely to occur satisfactorily. The neutrality of the neutral buffer means about pH 6.5 to 8.5. Examples of the buffer composition include a Tris buffer, a phosphate buffer, a HEPES buffer, and the like.

Further, prior to the first binding step, a blood sample may be subjected to a pretreatment. In the pretreatment, for example, antibodies such as IgG and IgM contained in the blood sample are removed. The blood sample contains antibodies derived from the sample that bind with the antibody immobilized to the carrier for use in the binding step. Therefore, by removing the antibodies derived from the sample prior to the binding step, it is possible to prevent the antibodies derived from the sample from binding with the antibody used in the binding step. The antibodies derived from the sample can be removed by bringing the blood sample into contact with carriers to which Protein G, Protein A, Protein L, an anti-IgG antibody, an anti-IgM antibody, an anti-IgA antibody, an anti-IgY antibody, an anti-IgD antibody, an anti-IgE antibody and the like are bound. In the present invention, in the case where the affinity purification is conducted twice consecutively, a pretreatment for a blood sample prior to the first binding step may not be conducted.

(First Washing Step)

Next, a bound body of the first antibody-immobilized carrier and the target Aβ related peptide obtained by the first binding step is washed with the use of a washing solution.

In the washing step, it is preferred first, washing is conducted by using a neutral buffer containing a surfactant as the washing solution, and then washing is conducted by using a neutral buffer not containing a surfactant as the washing solution.

As the neutral buffer containing a surfactant as the washing solution, those similar to the neutral buffer containing a surfactant as the binding solution described above can be used. First, by conducting washing with the use of the neutral buffer containing a surfactant, unnecessary components such as highly hydrophobic blood protein, lipid, and glycolipid are ordinarily removed. The neutrality of the neutral buffer is preferably pH closer to that of the body fluid, and for example, pH 6.5 to 8.5 is preferred, and pH 7.0 to 8.0 is more preferred. By washing with such a neutral buffer, it is possible to prevent the target Aβ related peptide in the antigen antibody bound body from being dissociated from the carrier in this washing step.

Then, it is preferred to conduct washing with a neutral buffer not containing a surfactant. By washing with a neutral buffer not containing a surfactant, inconvenience such as bubbling in the subsequent operation is easily prevented.

In the washing step, by subjecting the carrier surface to a fluid pressure of 0.01 to 500 MPa, preferably 0.05 to 300 MPa, more preferably 0.1 to 200 MPa of the washing solution, unnecessary components can be removed. If the fluid pressure is below the aforementioned range, a desired washing effect tends not to be obtained. If the fluid pressure exceeds the aforementioned range, the binding between the antibody and the bound target polypeptide may be cleaved. By conducting the washing in a higher pressure condition, it is possible to improve the efficiency of removing non-specific adsorbed substance on the antibody-immobilized carrier, and this contributes to improvement in sensitivity of analysis (improvement in S/N ratio) of the bound target polypeptide.

A specific technique for washing is not particularly limited. For example, in the case of a globular carrier, it can be washed by stirring in a washing liquid. In the case of a planar carrier, it can be washed by spraying a high-pressure washing liquid from a washing nozzle. More specifically, in order to wash a specific region on the planar carrier under high pressure, a washing nozzle having an inner diameter suited for the area of the region can be used. This nozzle is formed of, for example, a double tube in which the inner tube can be functioned exclusively for water injection for spraying the washing liquid onto the carrier surface, and the outer tube can be functioned exclusively for water ejection for sucking the washing liquid sprayed on the carrier surface.

(First Dissociating and Eluting Step)

Next, for the bound body of the first antibody-immobilized carrier and the target Aβ related peptide after washing, the target Aβ related peptide is dissociated from the antibody-immobilized carrier by using an acidic aqueous solution as an eluent.

In order to dissociate an antigen from an antibody to which the antigen is bound (antigen-antibody complex), an acidic aqueous solution is brought into contact with the antigen-antibody complex. In the present invention, the target Aβ related peptide is dissociated and eluted from the antibody-immobilized carrier to which the target Aβ related peptide is bound by using an acidic aqueous solution.

The acidic aqueous solution preferably contains a surfactant. When a surfactant is contained in the acidic aqueous solution, dissociation of the target Aβ related peptide from the carrier occurs efficiently. As a result, this contributes to improvement in recovery of the bound target Aβ related peptide. If the concentration of the surfactant is less than the CMC, the effect of the surfactant is not obtained, and the efficiency of dissociation of the target Aβ related peptide is not excellent. For example, by using an aqueous solution containing 0.1% DDM in 50 mM Glycine buffer (pH 2.8) , a higher elution efficiency is easily obtained. The acidity of the acidic aqueous solution means about pH 1 to 3.5.

Also, when the surfactant is contained in the acidic aqueous solution, it is effective for preventing the eluted target Aβ related peptide from being adsorbed to a tube, a test tube, a microplate or the like, and for suppressing loss of the target Aβ related peptide due to such adsorption.

Normally, the acidic aqueous solution containing the surfactant used for dissociation can be used also as an eluent to elute the target Aβ related peptide dissociated from the carrier. Alternatively, a person skilled in the art can select the eluent appropriately. In the case of conducting continuous Immunoprecipitation-Mass spectrometry (cIP-MS), in the first dissociating and eluting step, the acidic aqueous solution does not preferably contain an organic solvent so as not to deteriorate the reaction efficiency in the next second reaction step. In the case of conducting Immunoprecipitation-Mass spectrometry (IP-MS), a first eluate preferably contains an organic solvent.

In the dissociating step, by bringing the carrier surface into contact with the eluent, the target Aβ related peptide can be dissociated and eluted. The carrier may be stirred in the eluent as is necessary. In this manner, a first eluate is obtained. In the case of conducting Immunoprecipitation-Mass spectrometry (IP-MS), the first eluate may be subjected to mass spectrometry.

(Neutralizing Step)

The pH of the eluate is neutralized by adding a neutral buffer to the obtained first eluate, and thus a first purified solution with neutralized pH is obtained. In the neutralizing step, as the neutral buffer, those similar to the neutral buffer as the binding solution described above can be used. The neutral buffer preferably contains a surfactant. The neutrality of the neutral buffer is preferably pH closer to that of the body fluid, and for example, pH 6.5 to 8.5 is preferred, and pH 7.0 to 8.0 is more preferred. As the pH of the first purified solution, for example, pH 6.5 to 8.5 is preferred, and pH 7.0 to 8.0 is more preferred. By employing such a pH range, high reaction efficiency in the next second reaction step is easily obtained. Further, in the neutralizing step, the neutral buffer preferably does not contain an organic solvent so as not to deteriorate the reaction efficiency in the next second reaction step.

(Second Binding Reaction Step)

Next, the first purified solution is brought into contact with the second antibody-immobilized carrier, to bind the second antibody-immobilized carrier with the target Aβ related peptide contained in the first purified solution.

The first purified solution has already contained a binding solution by the aforementioned operation. However, a binding solution that is the same as that in the first binding reaction step, and is used in the ordinary immunoprecipitation method (IP) may further be added in this stage.

Preferably, the liquid amount of the first purified solution subjected to the second reaction step is smaller than the liquid amount of the liquid containing a biological sample (biological sample liquid containing the biological sample and a binding solution) subjected to the first reaction step. In an aspect of the present invention, when the liquid amount of the first purified solution subjected to the second reaction step is smaller than the liquid amount of the biological sample liquid subjected to the first reaction step (that is, the total liquid amount of the biological sample and the binding solution), the binding efficiency of the antibody with the target Aβ related peptide in the second reaction step is elevated, and loss of the target Aβ related peptide can be further reduced. That is, in many cases, since the binding rate of the antibody with the target Aβ related peptide in the affinity purification is not 100%, loss of the target Aβ related peptide occurs more or less every time the affinity purification is conducted. The impurity substances are much reduced by conducting the affinity purification twice consecutively as compared with the case of conducting the affinity purification only once; however, the target Aβ related peptide is simultaneously reduced as well. For this reason, in order to reduce loss of the target Aβ related peptide by increasing the binding efficiency of the antibody with the target Aβ related peptide in the second time, it is preferred to reduce the reaction solution amount (namely, the liquid amount of the first purified solution) in the second affinity purification.

Preferably, the liquid amount of the first purified solution subjected to the second reaction step is made smaller as compared with the liquid amount of the biological sample liquid subjected to the first reaction step (namely, the total liquid amount of the biological sample and the binding solution) . The liquid amount of the first purified solution subjected to the second reaction step may be, for example, about 0.1 to 50%, preferably about 0.5 to 20%, more preferably about 1 to 10% by volume, on the basis of the liquid amount of the biological sample liquid subjected to the first reaction step. This can be achieved in such a manner that the liquid amount of the first purified solution is reduced by reducing the amount of the first eluate with reduction of the amount of the acidic solution used in the first eluting step, by reducing the amount of the neutral buffer used in the neutralizing step, or the like.

Preferably, the amount of the second antibody-immobilized carrier in the second reaction step is smaller than the amount of the first antibody-immobilized carrier in the first reaction step. In an aspect of the present invention, when the amount of the second antibody-immobilized carrier in the second reaction step is smaller than the amount of the first antibody-immobilized carrier in the first reaction step, a liquid amount of the eluate which is to be a sample solution at the time of measurement by mass spectrometry (second purified solution) can be made small, with the result that the target Aβ related peptide is further concentrated, and can be detected with high sensitivity. That is, the target Aβ related peptide is further concentrated and detection with highly sensitivity can be conducted by using a smaller amount of the sample solution at the time of measurement by mass spectrometry. For reducing the liquid amount of the eluate which is to be a sample solution at the time of measurement by mass spectrometry, it is preferred to reduce the amount of the antibody-immobilized carrier used in the second affinity purification. It is also effective to reduce contamination with non-specifically adsorbed substances or impurity substances derived from antibody-immobilized carriers.

The amount of the second antibody-immobilized carrier in the second reaction step may be, for example, about 1 to 50%, preferably about 5 to 25% by surface area of the carrier, on the basis of the amount of the first antibody-immobilized carrier in the first reaction step. When the first antibody-immobilized carrier and the second antibody-immobilized carrier are the same carrier, the surface area of the carrier is synonymous to the weight of the carrier, and the number of carriers.

(Second Washing Step)

A bound body of the second antibody-immobilized carrier and the target Aβ related peptide obtained in the second binding step is washed with the use of a washing solution.

In the washing step, it is preferred first, washing is conducted by using a neutral buffer containing a surfactant as the washing solution, and then washing is conducted by using a neutral buffer not containing a surfactant as the washing solution.

As the neutral buffer containing a surfactant as the washing solution, those similar to the neutral buffer containing a surfactant as the binding solution described above can be used. First, by conducting washing with the use of the neutral buffer containing a surfactant, unnecessary components such as highly hydrophobic blood protein, lipid, and glycolipid are ordinarily removed. The neutrality of the neutral buffer is preferably pH closer to that of the body fluid, and for example, pH 6.5 to 8.5 is preferred, and pH 7.0 to 8.0 is more preferred. By washing with such a neutral buffer, it is possible to prevent the target Aβ related peptide in the antigen antibody bound body from being dissociated from the carrier in this washing step.

Then, it is preferred to conduct washing with a neutral buffer not containing a surfactant. By washing with a neutral buffer not containing a surfactant, inconvenience such as bubbling in the subsequent operation is easily prevented. Further, it is possible to reduce ionization suppression (ion suppression) due to contamination with a surfactant in the detecting step.

In the washing step, by subjecting the carrier surface to a fluid pressure of 0.01 to 500 MPa, preferably 0.05 to 300 MPa, more preferably 0.1 to 200 MPa of the washing solution, unnecessary components can be removed. If the fluid pressure is below the aforementioned range, a desired washing effect tends not to be obtained. If the fluid pressure exceeds the aforementioned range, the binding between the antibody and the bound target Aβ related peptide may be cleaved. By conducting the washing in a higher pressure condition, it is possible to improve the efficiency of removing non-specific adsorbed substance on the antibody-immobilizing carrier, and this contributes to improvement in sensitivity of analysis (improvement in S/N ratio) of the bound target Aβ related peptide.

A specific technique for washing is similar to that described in the first washing step, and is not particularly limited.

(Second Dissociating and Eluting Step)

Next, for the bound body of the second antibody-immobilized carrier and the target Aβ related peptide after washing, the target Aβ related peptide is dissociated from the antibody-immobilized carrier by using an acidic aqueous solution as an eluent.

In order to dissociate an antigen from an antibody to which the antigen is bound (antigen-antibody complex), an acidic aqueous solution is brought into contact with the antigen-antibody complex. In an aspect of the present invention, the target polypeptide is dissociated and eluted from the antibody-immobilized carrier to which the target polypeptide is bound by using an acidic aqueous solution. The acidic aqueous solution preferably contains an organic solvent. When an organic solvent is contained in the acidic aqueous solution, dissociation of the target Aβ related peptide from the carrier occurs efficiently. As a result, this contributes to improvement in recovery of the bound target Aβ related peptide. Examples of the organic solvent used in this case include organic solvents that mingle with water at an arbitrary ratio, such as acetonitrile, acetone, methanol, ethanol, isopropanol, chloroform and the like. While the concentration of the organic solvent in the acidic aqueous solution is not particularly limited, it is for example about 10 to 90% (v/v), preferably 20 to 80% (v/v), and more preferably about 25 to 70% (v/v). When the concentration of the organic solvent in the acidic aqueous solution falls within the aforementioned range, dissociation of the target Aβ related peptide from the carrier occurs efficiently. This contributes to improvement in sensitivity of analysis (improvement in S/N ratio) of the bound target Aβ related peptide. If the concentration of the organic solvent is less than 10% (v/v), the effect of the organic solvent is not obtained, and the efficiency of dissociation of the target polypeptide is not excellent. For example, by using an aqueous solution containing 70% (v/v) acetonitrile in 5 mM acetic acid, a higher elution efficiency is easily obtained. The acidity of the acidic aqueous solution means about pH 1 to 3.5.

Normally, the acidic aqueous solution containing the organic solvent used for dissociation can be used also as an eluent to elute the target Aβ related peptide dissociated from the carrier. Alternatively, a person skilled in the art can select the eluent appropriately.

In the dissociating step, by bringing the carrier surface into contact with the eluent, the target Aβ related peptide can be dissociated and eluted. The carrier may be stirred in the eluent as is necessary. In this manner, a second purified solution is obtained.

(Detecting Step)

Next, the target Aβ related peptide contained in the obtained second purified solution is detected by mass spectrometry. The mass spectrometry is preferably mass spectrometry such as matrix-assisted laser desorption/ionization (MALDI) mass spectrometry or electrospray ionization (ESI) mass spectrometry. For example, a MALDI-TOF (matrix-assisted laser desorption/ionization-time of flight) mass spectrometer, a MALDI-IT (matrix-assisted laser desorption/ionization-ion trap) mass spectrometer, a MALDI-IT-TOF (matrix-assisted laser desorption/ionization-ion trap-time of flight) mass spectrometer, a MALDI-FTICR (matrix-assisted laser desorption/ionization-Fourier transformation ion cyclotron resonance) mass spectrometer, an ESI-QqQ (electrospray ionization - triple quadrupole) mass spectrometer, an ESI-Qq-TOF (electrospray ionization-tandem quadrupole-time of flight) mass spectrometer, an ESI-FTICR (electrospray ionization-Fourier transformation ion cyclotron resonance) mass spectrometer or the like can be employed.

A matrix and a matrix solvent can be appropriately determined by a person skilled in the art depending on the analysis subject (Aβ related peptide).

As the matrix, for example, α-cyano-4-hydroxycinnamic acid (CHCA), 2,5-dihydroxybenzoic acid (2,5-DHB), sinapic acid, 3-aminoquinoline (3-AQ) or the like can be used.

The matrix solvent can be selected from the group consisting of, for example, acetonitrile (ACN), trifluoroacetic acid (TFA), methanol, ethanol and water, and used. More specifically, an ACN-TFA aqueous solution, an ACN aqueous solution, methanol-TFA aqueous solution, a methanol aqueous solution, an ethanol-TFA aqueous solution, an ethanol solution or the like can be used. The concentration of ACN in the ACN-TFA aqueous solution can be, for example, 10 to 90% by volume, the concentration of TFA can be, for example, 0.05 to 1% by volume, preferably 0.05 to 0.1% by volume.

The matrix concentration can be, for example, 0.1 to 50 mg/mL, preferably 0.1 to 20 mg/mL, or 0.3 to 20 mg/mL, further preferably 0.5 to 10 mg/mL.

In the case of employing MALDI mass spectrometry as a detecting system, a matrix additive (comatrix) is preferably used together. The matrix additive can be appropriately selected by a person skilled in the art depending on the analysis subject (polypeptides) and/or the matrix. For example, as the matrix additive, a phosphonic acid group-containing compound can be used. Specific examples of a compound containing one phosphonic acid group include phosphonic acid, methylphosphonic acid, phenylphosphonic acid, 1-naphthylmethylphosphonic acid, and the like. Examples of a compound containing two or more phosphonic acid groups include methylenediphosphonic acid (MDPNA), ethylenediphosphonic acid, ethane-1-hydroxy-1,1-diphosphonic acid, nitrilotriphosphonic acid, ethylenediaminetetraphosphonic acid, and the like. Among the aforementioned phosphonic acid group-containing compounds, compounds having two or more, preferably two to four phosphonic acid groups in one molecule are preferred.

The use of the phosphonic acid group-containing compound is useful, for example, when metal ions of the washing solution remaining on the surface of the antibody-immobilized carrier are contaminated into the eluate after the dissociating step. The metal ions adversely affect on the background in the mass spectrometry. The use of the phosphonic acid group-containing compound is effective for suppressing such an adverse affect.

Besides the aforementioned matrix additive, a more common additive, for example, a substance that is selected from the group consisting of ammonium salts and organic bases may be used.

The matrix additive can be prepared as a solution of 0.1 to 10 w/v %, preferably 0.2 to 4 w/v % in water or in a matrix solvent. The matrix additive solution and the matrix solution can be mixed in a volume ratio of, for example, 1:100 to 100:1, preferably 1:10 to 10:1.

(Measurement Method of Aβ Related Peptide by Immunoassay)

Furthermore, a fourth aspect of the present invention is a method for measuring an Aβ related peptide in a biological sample, the method comprising:

a reaction step of bringing a liquid containing a biological sample into contact with the above-mentioned monoclonal antibody, to bind an Aβ related peptide in the biological sample with the monoclonal antibody; a step of detecting the Aβ related peptide binding with the monoclonal antibody by a method selected from the group consisting of a sandwich immunoassay method, a direct ELISA, an indirect ELISA, a competitive ELISA, a western blotting, an immunohistochemistry, a flow cytometry, an immunoprecipitation, an affinity chromatography, and an immunocytochemistry.

The above reaction step and the detecting step may be carried out by using the known method to a person skilled in the art. For example, as to a sandwich immunoassay method, in the case of a sandwich ELISA (Enzyme-Linked ImmunoSorbent Assay) utilizing an enzyme as a labeling substance, it is advisable that the above-mentioned anti-Aβ monoclonal antibody, as a first antibody, is used as an immobilized antibody (a capture antibody); and another antibody against the target Aβ related peptide, as a second antibody, is used as a detection antibody (a labeled antibody).

The sandwich immunoassay method may use the sandwich ELISA utilizing an enzyme as a labeling substance, and furthermore, a radio immunoassay method (RIA) utilizing a radioisotope, a chemiluminescent immunoassay method (CIA) utilizing a chemiluminescent substance, a fluorescent immunoassay method (FIA) utilizing a fluorescent substance, an electro-chemiluminescent immunoassay method (ECLIA) utilizing a metal complex, a bioluminescent immunoassay method (BLIA) utilizing a bioluminescent substance such as a luciferase, an immuno-PCR comprising amplifying a nucleic acid that labeled an antibody by PCR and detecting the nucleic acid, a turbidimetric immunoassay method (TAI) detecting turbidity occurred by forming an immunocomplex, a latex agglutination turbidimetric method (LA) detecting a latex aggregated by forming an immunocomplex, an immunochromatography assay utilizing a reaction on a cellulose membrane, and the like.

The present invention provides a kit for measuring an Aβ related peptide in blood plasma by IP-MS, said kit comprising the above-mentioned novel anti-Aβ antibody clone 16-10E as a constituent component. More specifically, the present invention provides a kit for measuring an Aβ related peptide, said kit comprising an antibody-immobilized carrier, as a constituent component, in which the anti-Aβ antibody (clone 16-10E) is bound to the above-mentioned carrier.

Furthermore, the kit can contain various components used for operations in the IP-MS (including also the cIP-MS), such as a diluting solution for use of a preparation of sample solution, a washing solution, and the like.

EXAMPLES

Hereinafter, the present invention will be described specifically with reference to examples, but is not limited to these examples. In the following, the amount of a matter indicated by % is based on weight when the matter is solid, and based on volume when the matter is liquid unless otherwise indicated.

Each of the neutral surfactants is represented as an abbreviated name below.

n-Decyl-β-D-maltoside (DM)
n-Dodecyl-β-D-maltoside (DDM)
n-Nonyl-β-D-thiomaltoside (NTM)

Example 1: Preparation of Anti-Aβ Antibody

A synthetic peptide DAEFRHDSGYEVHHQKC (SEQ ID NO: 10; this sequence is equivalent to a sequence wherein Cys (C) is conjugated to Lys (K) at C terminal of Aβ1-16) was used.

A C-terminal Lys Cys of the synthetic peptide DAEFRHDSGYEVHHQKC was conjugated to a carrier protein KLH (Keyhole Limpet Hemocyanin) by using a divalent reactive reagent.

The obtained KLH conjugated synthetic peptide was emulsified by mixing with FCA (Freund's complete adjuvant) using a syringe, and injected (i.e., immunized) into a muscle of a tail joint of a BALB/c mouse in the amount of 200 μg per one mouse. After two weeks from the immunity, a blood test from the mouse was conducted, and it was confirmed that an antibody activity against Aβ was increased. And then, a blood collection from the mouse was conducted, and a lymph node of an iliac bone was collected from the mouse.

The cell fusion of the obtained lymphocytes and mouse myeloma was conducted in the presence of 50% of polyethylene glycol. The fused cells were dispensed onto four 96 well microplates to be cultured. After eight days from the cell fusion, the culture supernatant was sampled from the each well of the 96 well microplates, and a primary screening was conducted by ELISA, and furthermore, a secondary screening as to positive well was conducted by ELISA. The cell of the positive well selected by the screening was cloned by limiting dilution analysis. Thereafter, a primary screening and a secondary screening were conducted sequentially by ELISA, each hybridoma of the positive 6 clones was cryopreserved.

Figure 3:
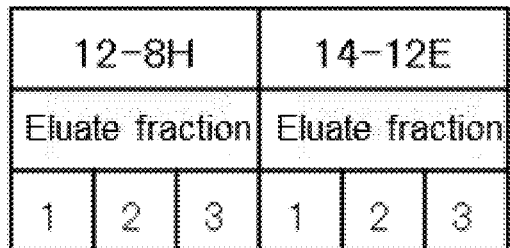
FIG. 3 shows the results of confirmation by SDS-PAGE after purifying the culture supernatant of the hybridoma (clone 12-8H, 14-12E) by the ammonium sulfate precipitation and Protein G, in Example 1.
Figure 3:
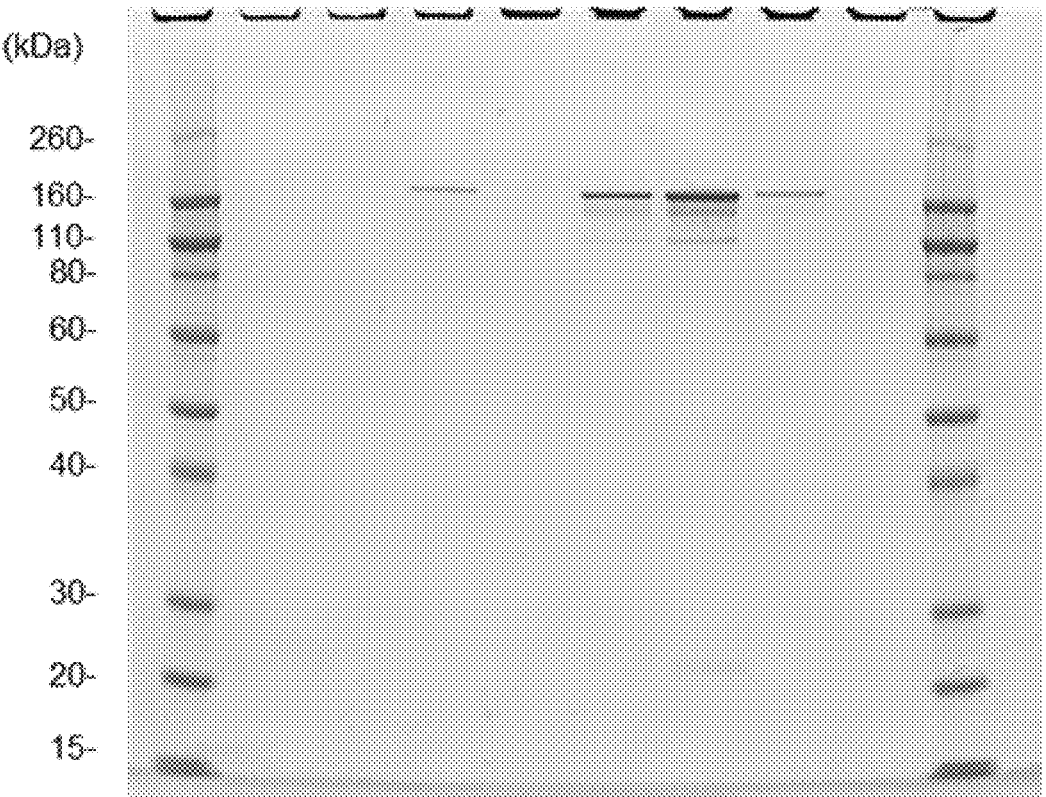
Figure 4:
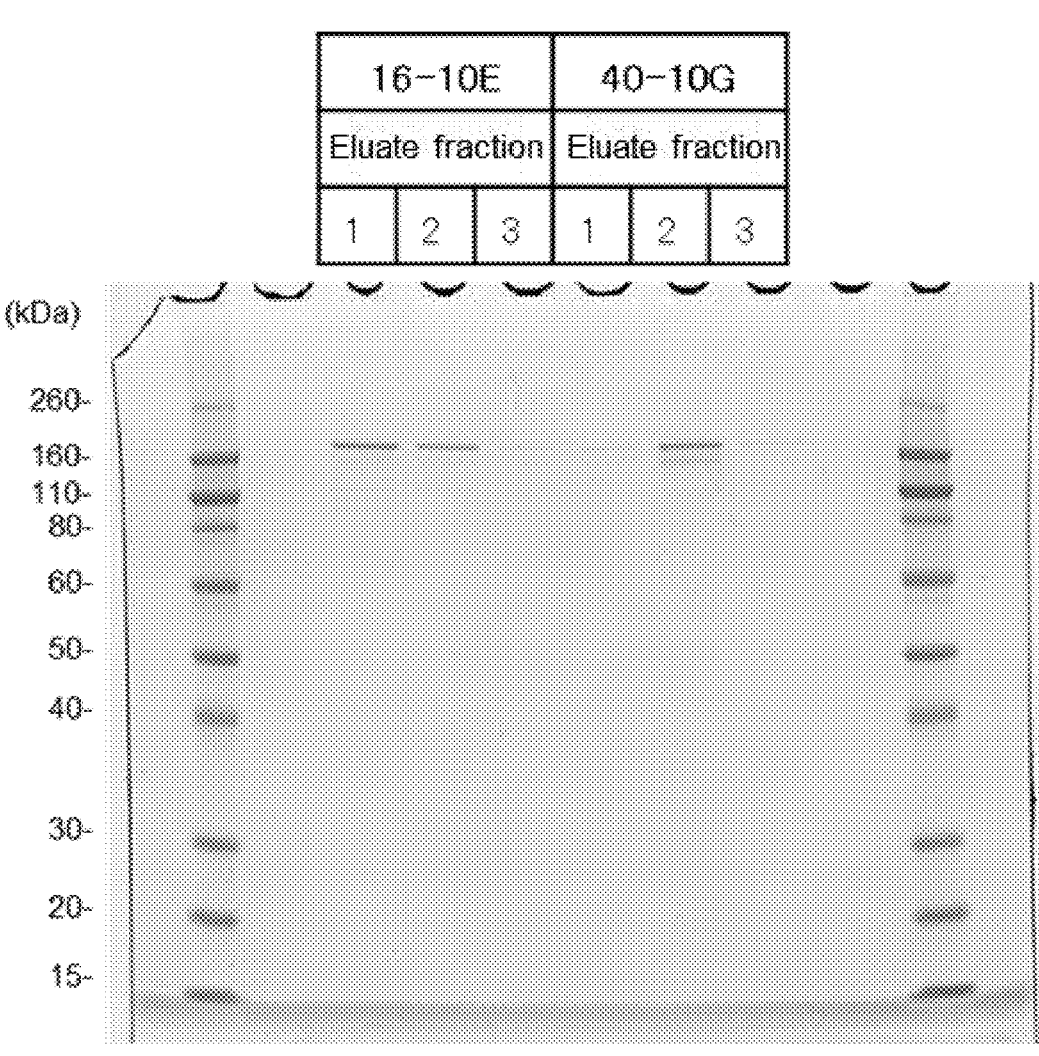
FIG. 4 shows the results of confirmation by SDS-PAGE after purifying the culture supernatant of the hybridoma (clone 16-10E, or 40-10G) by the ammonium sulfate precipitation and Protein G, in Example 1.

Thus obtained each hybridoma (clone 5-1D, 8-1F, 12-8H, 14-12E, 16-10E, or 40-10G) was cultured. An ammonium sulfate precipitation for each culture supernatant was conducted, and then, an antibody was purified by using Protein G. Confirmation by SDS-PAGE was conducted (FIGS. 2, 3, and 4) . As to the purified antibody, the Bradford assay was conducted to determine a quantity of protein.

FIGS. 2 to 4 show the results of confirmation by SDS-PAGE after purifying the culture supernatant of the hybridoma by the ammonium sulfate precipitation and Protein G. FIG. 2 shows the results of the hybridoma (clone 5-1D, 8-1F), FIG. 3 shows the results of the hybridoma (clone 12-8H, 14-12E) , and FIG. 4 shows the results of the hybridoma (clone 16-10E, 40-10G), respectively. Here, in each figure, "Eluate fraction 1, 2, and 3" indicates each eluate fraction obtained when Protein G affinity chromatography was conducted.

Example 2: IP-MS by Anti-Aβ Antibody

Aβ related peptides in human blood plasma were measured by using IP-MS that is a combination of an immunoprecipitation (IP) using an anti-Aβ monoclonal antibody and a mass spectrometry (MS).

In the IP, each of anti-Aβ antibody clones of 5-1D, 8-1F, 12-8H, 14-12E, 16-10E, and 40-10G was covalently bound with Dynabeads Epoxy (Thermo Fisher Scientific) as magnetic beads to produce antibody-immobilized beads, respectively. The thus obtained antibody-immobilized beads were used. And, further, antibody-immobilized beads produced by using a clone 6E10 (bioLegend) were used as a positive control. The clone 6E10 is an anti-Aβ antibody (IgG) recognizing the Aβ3-8 residues of Aβ related peptide as an epitope.

250 μL of a plasma in which Aβ1-40, Aβ1-42 and APP669-711 were spiked, and 250 μL of a reaction solution [800 mM GlcNAc, 0.2% (w/v) NTM, 0.2% (w/v) DDM, 300 mM NaCl, 100 mM Tris-HCl buffer (pH 7.4)] including an internal standard peptide were mixed. The resultant mixture was mixed with each of the above-mentioned antibody-immobilized beads [beads amount (beads weight): 291 μg] to carry out an antigen-antibody reaction at 4° C. for 1 hour (the first IP).

As the internal standard peptide, 11 pM Aβ1-38 that is a stable isotope-labeled (SIL) (referred to as SIL-Aβ1-38; manufactured by AnaSpec, San Jose, Calif., USA) was used. In SIL-β1-38, carbon atoms in Phe and Ile are substituted by $^{13}$C.

After the antigen-antibody reaction, the antibody beads were washed, and then, Aβ related peptides were eluted by using a Glycine buffer containing DDM (pH 2.8).

After the antigen-antibody reaction, the antibody-immobilized beads were washed with a first washing buffer [specifically, the beads were washed three times with 100 μL of a first washing buffer (0.1% DDM, 0.1% NTM, 50 mM Tris-HCl (pH 7.4), 150 mM NaCl), and twice with 50 μL of a 50 mM ammonium acetate buffer]. And then, the Aβ related peptides captured to the antibody-immobilized beads were eluted with a Glycine buffer containing DDM (50 mM Glycine buffer containing 0.1% DDM, pH 2.8). To the obtained eluate, a Tris buffer containing DDM [800 mM GlcNAc, 0.2% (w/v) DDM, 300 mM NaCl, 300 mM Tris-HCl buffer (pH 7.4)] was added to neutralize the solution pH as neutral (pH 7.4). And thereafter, the neutral eluate was again brought into contact with the each of the antibody-immobilized beads [beads amount (beads weight) : 73 μg] to carryout an antigen-antibody reaction at 4° C. for 1 hour (the second IP). Then, the antibody-immobilized beads were washed with a second washing buffer [specifically, the beads were washed five times with 100 μL of a second washing buffer (0.1% DDM, 150 mM Tris-HCl (pH 7.4), 150 mM NaCl), twice with 50 μL of a 50 mM ammonium acetate buffer, and once with 30 μL of pure water]. And then, the Aβ related peptides captured to the antibody-immobilized beads was eluted with an eluent (5 mM HCl, 0.1 mM Methionine, 70% (v/v) acetonitrile). In this manner, each eluate containing the Aβ related peptides was obtained by the two step IP operation.

As a matrix for Linear TOF, α-cyano-4-hydroxycinnamic acid (CHCA) was used. A matrix solution was prepared by dissolving 1 mg of CHCA in 1 mL of 70% (v/v) acetonitrile. As a matrix additive, 0.4% (w/v) methanediphosphonic acid (MDPNA) was used. Equivalent amounts of a 1 mg/mL CHCA solution and 0.4% (w/v) MDPNA were mixed to obtain a matrix/matrix additive solution [0.5 mg/mL CHCA/ 0.2% (w/v) MDPNA].

In advance, 0.5 μL of the matrix/matrix additive solution was added dropwise on each well of a μFocus MALDI plate™ 900 μm (Hudson Surface Technology, Inc., Fort Lee, NJ) and dried.

The each eluate after the IP operation was added dropwise on the 4 wells of the μFocus MALDI plate™ 900 μm and dried.

The mass spectrum data were acquired by Linear TOF in a positive ion mode by using AXIMA Performance (Shimadzu/KRATOS, Manchester, UK). A m/z value of Linear TOF was indicated by an average mass of peaks. The m/z value was calibrated by using human angiotensin II, human ACTH fragment 18-39, bovine insulin oxidized beta-chain, and bovine insulin as external standards.

Figure 5:
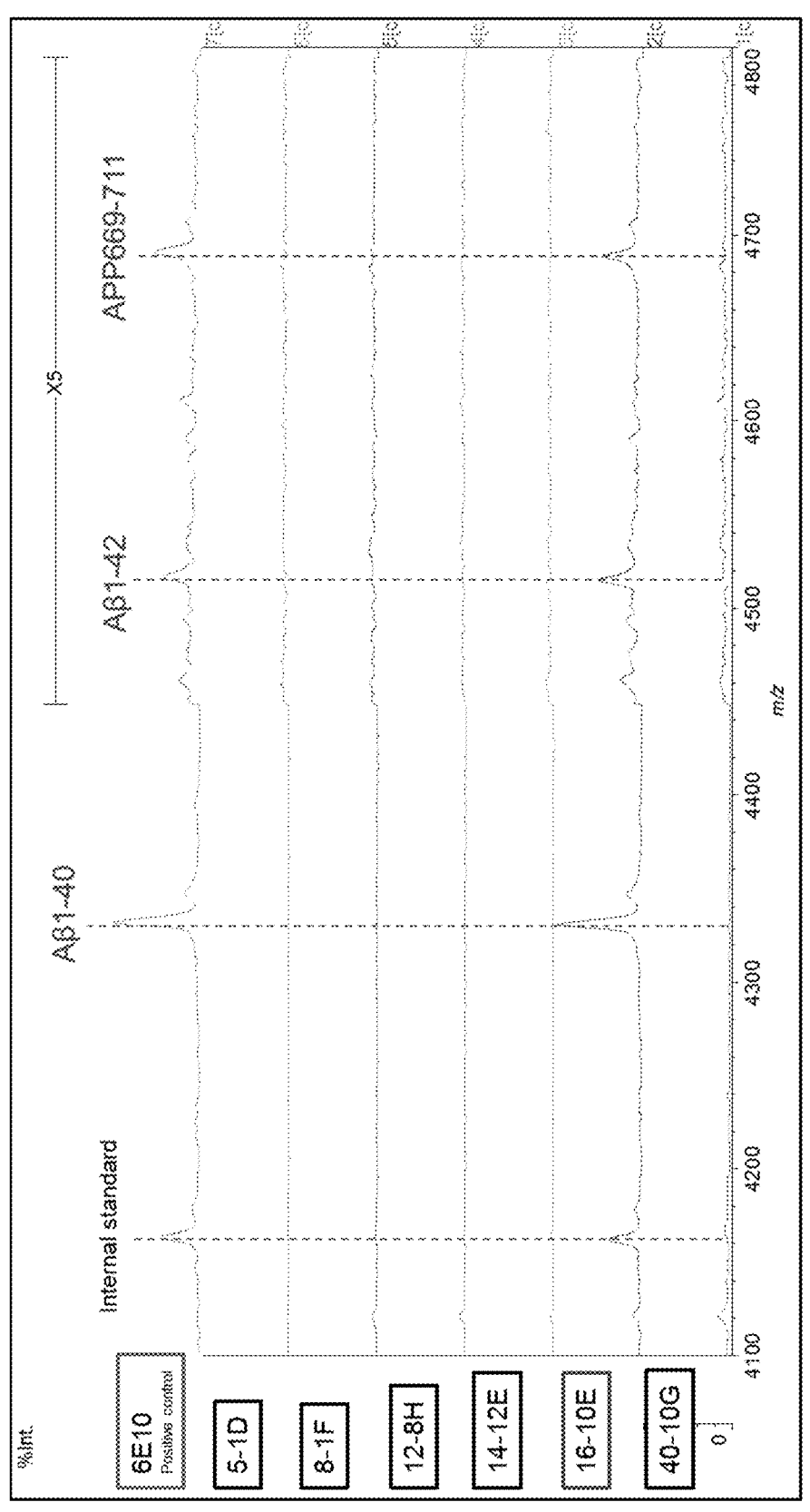
FIG. 5 shows the results of IP-MS measurement with the use of 6E10 as the positive control, and the obtained 6 clones. The horizontal axis indicates m/z, and the vertical axis indicates relative intensity of ion. Each IP-MS spectrum shows the results as to anti-Aβ antibody clone 6E10, 5-1D, 8-1F, 12-8H, 14-12E, 16-10E, and 40-10G in order from the top, in Example 2.

These results are shown in FIG. 5. FIG. 5 shows the results of IP-MS measurement with the use of 6E10 as the positive control, and the obtained 6 clones. The horizontal axis indicates m/z, and the vertical axis indicates relative intensity of ion. Each MS spectrum shows the results as to the anti-Aβ antibody clone 6E10, 5-1D, 8-1F, 12-8H, 14-12E, 16-10E, and 40-10G in order from the top.

Table 1 shows amino acid sequences of Aβ related peptides. Only when 16-10E was used for IP among anti-Aβ antibody clone 5-1D, 8-1F, 12-8H, 14-12E, 16-10E, and 40-10G produced in Example 1, the obtained spectrum indicated as equivalent to the spectrum with the use of 6E10 as the positive control. In the each spectrum with the use of the other 5 clones, Aβ related peptides peaks were not detected in the displayed mass range (m/z value: 4100 to 4800). From the results, it is found that 16-10E is a useful clone for measuring Aβ related peptides in blood plasma by IP-MS.

TABLE 1

| SEQ ID NO. | Peptide Name | Sequence |
|---|---|---|
| 1 | Aβ3-8 | EFRHDS |
| 2 | Aβ1-37 | DAEFRHDSGYEVHHQKLVFFAEDVGSNKGAIIG |

TABLE 1-continued

| SEQ ID NO. | Peptide Name | Sequence |
|---|---|---|
| | | LMVG |
| 3 | Aβ1-38 | DAEFRHDSGYEVHHQKLVFFAEDVGSNKGAIIG LMVGG |
| 4 | Aβ1-39 | DAEFRHDSGYEVHHQKLVFFAEDVGSNKGAIIG LMVGGV |
| 5 | Aβ1-40 | DAEFRHDSGYEVHHQKLVFFAEDVGSNKGAIIG LMVGGVV |
| 6 | Aβ1-42 | DAEFRHDSGYEVHHQKLVFFAEDVGSNKGAIIG LMVGGVVIA |
| 7 | APP669-709 (Aβ-3-38) | VKMDAEFRHDSGYEVHHQKLVFFAEDVGSNKGA IIGLMVGG |
| 8 | APP669-710 (Aβ-3-39) | VKMDAEFRHDSGYEVHHQKLVFFAEDVGSNKGA IIGLMVGGV |
| 9 | APP669-711 (Aβ-3-40) | VKMDAEFRHDSGYEVHHQKLVFFAEDVGSNKGA IIGLMVGGVV |

Example 3: IP-MS Evaluation by Changing Used Amount of Antibody Beads Using 16-10E

Example 3-1: IP-MS by Changing Amount of 16-10E Antibody Beads in First IP

The hybridoma 16-10E was expansively cultured in a normal growth medium, and then, was acclimatized in a serum-free culture medium. And thereafter, the hybridoma was gradually expansively cultured, and finally the hybridoma was cultured in 300 mL. A culture supernatant was collected at the time when the number of live cells was 20% or less. The obtained culture supernatant was purified by using protein A column, and was dialyzed with PBS. The resultant antibody solution was aseptically filtered, and a portion of the filtrate was taken as a sample to be measured the absorbance of 280 nm. A concentration of the antibody was calculated.

The purified clone 16-10E antibody solution was brought into contact with Dynabeads Epoxy (Thermo Fisher Scientific), and the 16-10E antibody was covalently bound with the Dynabeads Epoxy to produce the antibody-immobilized beads. And, further, antibody-immobilized beads produced by using a clone 6E10 were used as a comparative control.

250 μL of a commercially available plasma and 250 μL of a reaction solution including an internal standard peptide (SIL-Aβ1-38) were mixed. The resultant mixture was mixed with each of the above-mentioned antibody-immobilized beads to carry out an antigen-antibody reaction at 4° C. for 1 hour (the first IP). The 16-10E antibody beads amount (beads weight) used in the first IP was changed in four different amounts of 145, 291, 582, and 1164 μg. The 6E10 antibody-immobilized beads amount used in the first IP was 291 μg.

After the antigen-antibody reaction, the antibody-immobilized beads were washed with a first washing buffer [specifically, the beads were washed once with 100 μL of a first washing buffer (0.1% DDM, 0.1% NTM, 50 mM Tris-HCl (pH 7.4) , 150 mM NaCl) , and once with 50 μL of a 50 mM ammonium acetate buffer] . And then, the Aβ related peptides captured to the antibody-immobilized beads were eluted with a Glycine buffer containing DDM (50 mM Glycine buffer containing 0.1% DDM, pH 2.8). To the obtained eluate, a Tris buffer containing DDM [800 mM GlcNAc, 0.2% (w/v) DDM, 300 mM NaCl, 300 mM Tris-HCl buffer (pH 7.4)] was added to neutralize the solution pH as neutral (pH 7.4). And thereafter, the neutral eluate was again brought into contact with the each of the antibody beads of the same clone to carry out an antigen-antibody reaction at 4° C. for 1 hour (the second IP) . In the second IP step, both of the 16-10E antibody beads amount used (beads weight) and the 6E10 antibody beads amount used (beads weight) were fixed as 73 pg. Then, the antibody-immobilized beads were washed with a second washing buffer [specifically, the beads were washed twice with 100 μL of a second washing buffer (0.1% DDM, 150 mM Tris-HCl (pH 7.4), 150 mM NaCl) , once with 50 μL of a 50 mM ammonium acetate buffer, and once with 30 μL of pure water]. And then, the Aβ related peptides captured to the antibody-immobilized beads was eluted with an eluent (5 mM HCl, 0.1 mM Methionine, 70% (v/v) acetonitrile). In this manner, each eluate containing the Aβ related peptides was obtained by the two step IP operation.

In the same manner as in Example 2, in advance, 0.5 μL of the matrix/matrix additive solution was added dropwise on each well of a μFocus MALDI plate™ 900 μm (Hudson Surface Technology, Inc., Fort Lee, NJ) and dried.

The each eluate after the IP operation was added dropwise on the 4 wells of the μFocus MALDI plate™ 900 μm and dried.

In the same manner as in Example 2, the mass spectrum data were acquired.

These results are shown in FIG. 6. FIG. 6 shows IP-MS spectra by changing amount of the 16-10E antibody-immobilized beads in the first IP. The 6E10 antibody-immobilized beads were as the comparative control. The horizontal axis indicates m/z, and the vertical axis indicates relative intensity of ion. Each IP-MS spectrum shows the results as to the anti-Aβ antibody clone 6E10 (control, beads amount in the first IP: 291 μg), and the anti-Aβ antibody clone 16-10E (beads amount in the first IP: 1164, 582, 291, or 145 μg) in order from the top. The antibody beads amounts used are as indicated at the Table in the FIG. 6, and are indicated as beads weight.

From these results, it can be confirmed that even if the amount of the 16-10E antibody-immobilized beads was changed in the first IP, equivalent mass spectra were obtained from any amounts of the 16-10E antibody-immobilized beads, and all Aβ related peptides that were detected by the 6E10 antibody-immobilized beads were detected.

Example 3-2: IP-MS by Changing Amount of 16-10E Antibody Beads in Second IP

IP-MS by using the 16-10E antibody-immobilized beads were carried out in the same manner as in Example 3-1, except for the amount of the antibody-immobilized beads used. In the first IP, both of the 16-10E antibody-immobilized beads amount used and the 6E10 antibody-immobilized beads amount used were fixed as 291 μg. In the second IP, the 16-10E antibody beads amount used was changed in four different amounts of 18, 36, 73, and 145 μg. The 6E10 antibody beads amount used in the second IP was 73 μg.

Figure 7:
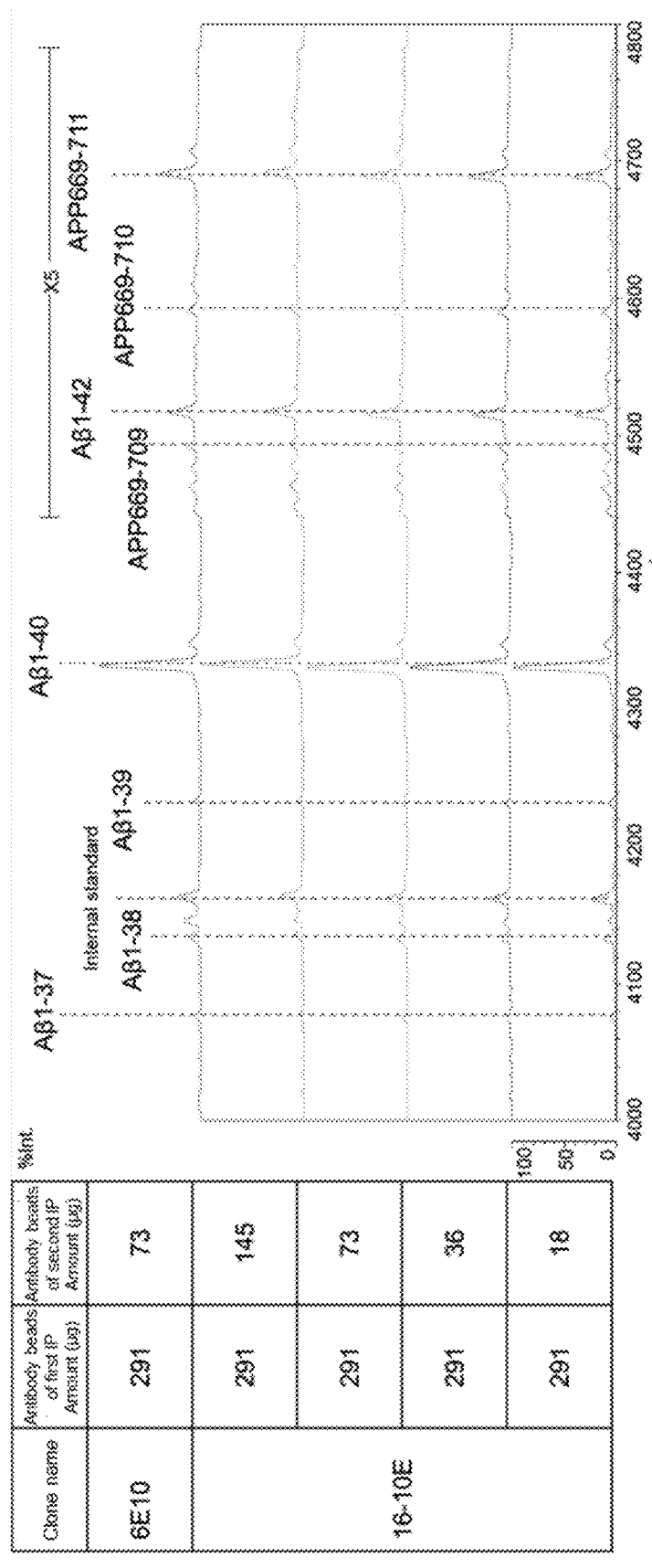
FIG. 7 shows IP-MS spectra by changing amount of the 16-10E antibody-immobilized beads in the second IP. The horizontal axis indicates m/z, and the vertical axis indicates relative intensity of ion. Each IP-MS spectrum shows the results as to the anti-Aβ antibody clone 6E10 (control, beads amount in the second IP: 73 μg), and the anti-Aβ antibody clone 16-10E (beads amount in the second IP: 145, 73, 36, or 18 μg) in order from the top. The antibody beads amounts used are as indicated at the Table in the FIG. 7, and are indicated as beads weight, in Example 3-2.

These results are shown in FIG. 7. FIG. 7 shows IP-MS spectra by changing amount of the 16-10E antibody-immobilized beads in the second IP. The 6E10 antibody-immobilized beads were as the comparative control. The horizontal axis indicates m/z, and the vertical axis indicates relative intensity of ion. Each IP-MS spectrum shows the results as to the anti-Aβ antibody clone 6E10 (control, beads amount in the second IP: 73 μg), and the anti-Aβ antibody clone 16-10E (beads amount in the second IP: 145, 73, 36, or 18 μg) in order from the top. The antibody beads amounts used are as indicated at the Table in the FIG. 7, and are indicated as beads weight.

From these results, it can be confirmed that even if the amount of the 16-10E antibody-immobilized beads was changed in the second IP, equivalent mass spectra were obtained from any amounts of the 16-10E antibody-immobilized beads, and all Aβ related peptides that were detected by the 6E10 antibody-immobilized beads were detected.

As shown in Example 3-1 and Example 3-2, it is revealed that even if the used amount of the 16-10E antibody beads was changed, the 16-10E antibody beads can detect the Aβ related peptides in blood plasma as with the 6E10 antibody beads.

Example 4: Aβ Reactivity Difference Between Clones 16-10E and 6E10

An Aβ3-8 peptide (SEQ ID NO: 1) solution (10, 100 nmol/mL) was added to each well of a 96 well plate in an amount of 50 μL, and incubated at 4° C. overnight to conduct an immobilization. Further, a well on which an immobilization of Aβ3-8 peptide is not conducted was also prepared (that is, no antigen). And then, the Aβ3-8 peptide solution in the each well was removed, and a blocking was conducted. And thereafter, a washing was conducted with PBS-Tween. The clone 16-10E antibody (2 μg/mL) obtained in Example 3 was added to each well in an amount of 50 μL, and incubated at 4° C. for 1 hour, and then, a washing was conducted with PBS-Tween. An HRP-labeled anti-mouse IgG-Fc solution was added to each well in an amount of 50 μL, and incubated at 4° C. for 1 hour. And thereafter, a washing was conducted with PBS-Tween. An ELISA POD Substrate TMB Kit (Nacalai) was added to each well in an amount of 100 μL, and an incubation in the dark for 30 minutes was conducted to develop a color. 100 μL of 2N sulfuric acid was added to stop the reaction of the color development. The absorbance of main wavelength 450 nm/sub wavelength 650 nm was measured by a microplate reader.

Figure 8:
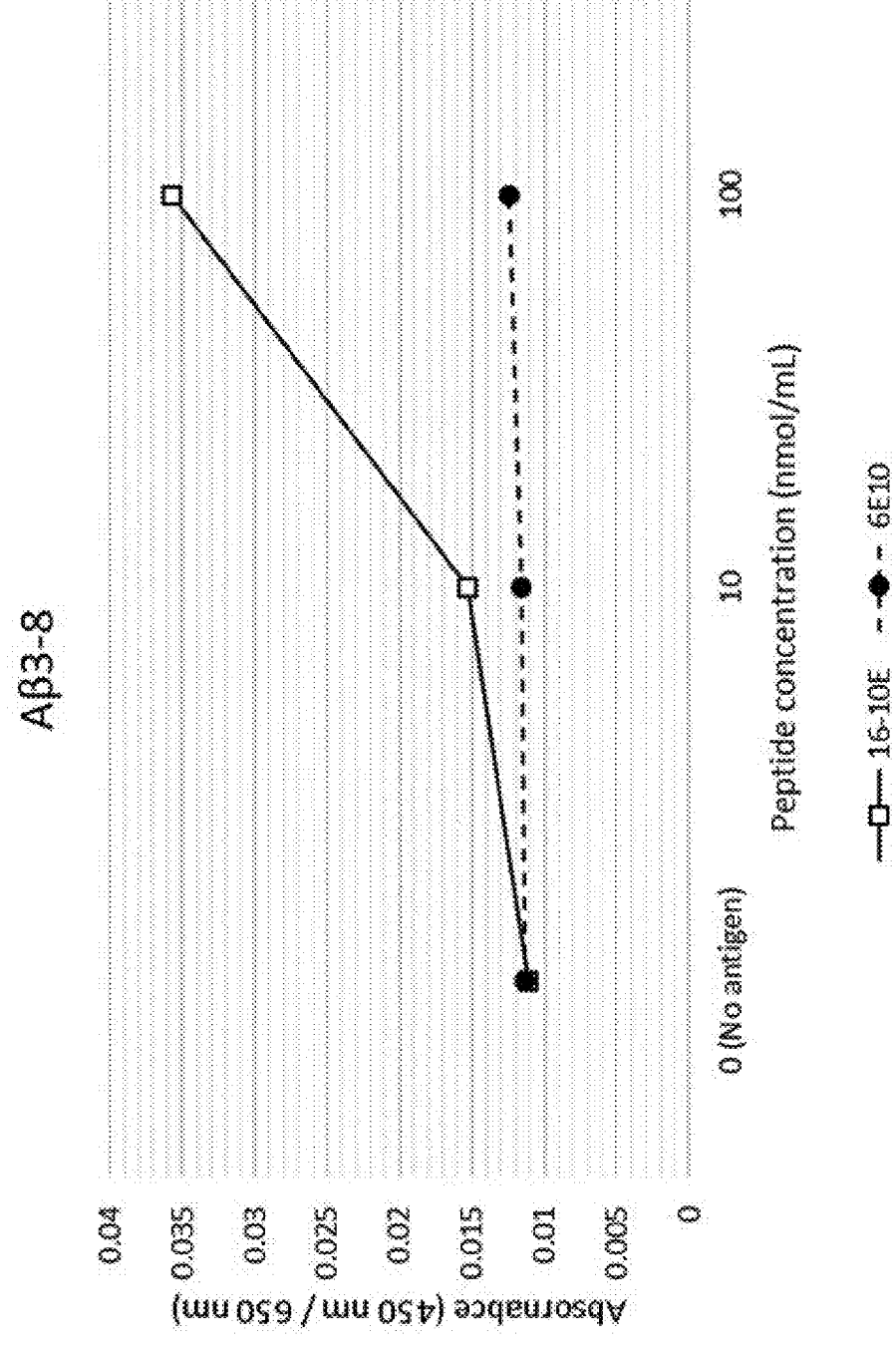
FIG. 8 is a graph showing the results of a direct ELISA for Aβ3-8 peptide by using the clone 16-10E antibody and the clone 6E10 antibody, respectively. The horizontal axis indicates the Aβ3-8 concentration (nmol/mL), and the vertical axis indicates the absorbance of main wavelength 450 nm/sub wavelength 650 nm measured by the microplate reader, in Example 4.

These results are shown in FIG. 8. FIG. 8 is a graph showing the results of a direct ELISA for Aβ3-8 by using the clone 16-10E antibody and the clone 6E10 antibody, respectively. The horizontal axis indicates the Aβ3-8 concentration (nmol/mL), and the vertical axis indicates the absorbance of main wavelength 450 nm/sub wavelength 650 nm measured by the microplate reader.

The results indicate that the clone 16-10E give a high absorbance of the well on which Aβ3-8 was immobilized, and therefore, the clone 16-10E has a reactivity with Aβ3-8.

On the other hand, the same experiment was carried out in the same manner as in the above, except that the clone 6E10 was used instead of the clone 16-10E, and the absorbance of each well of main wavelength 450 nm/sub wavelength 650 nm was measured. The results reveal that the clone 6E10 give an absorbance with equivalent level to that of the well on which Aβ3-8 was not immobilized, and therefore, the clone 6E10 has no reactivity with Aβ3-8. That is, the clone 6E10 is used as an antibody that recognizes the Aβ3-8 of an Aβ related peptide as an epitope, however, it is revealed that the clone 6E10 has no reactivity with Aβ3-8 peptide itself.

From these results, it is revealed that there is a difference in reactivity between the clone 16-10E and the clone 6E10 against Aβ3-8 peptide.

The clone 16-10E is a novel monoclonal antibody that recognizes Aβ3-8 peptide.

(1) A monoclonal antibody that recognizes an Aβ related peptide, and is produced by a hybridoma deposited under the accession number NITE BP-02998 at the NITE Patent Microorganisms Depositary of the National Institute of Technology and Evaluation.

(2) An antibody-immobilized carrier that includes a carrier and the monoclonal antibody according to the above item (1) bound to the carrier.

(3) A kit for measuring an Aβ related peptide, comprising the antibody-immobilized carrier according to the above item (2).

(4) A hybridoma deposited under the accession number NITE BP-02998 at the NITE Patent Microorganisms Depositary of the National Institute of Technology and Evaluation.

(5) The hybridoma according to the above item (4), having an ability to produce a monoclonal antibody that recognizes an Aβ related peptide.

(6) A method for measuring an Aβ related peptide in a biological sample, the method comprising:

a reaction step of bringing a liquid containing a biological sample into contact with an antibody-immobilized carrier that includes a carrier and the monoclonal antibody according to the above item (1) bound to the carrier, to bind an Aβ related peptide in the biological sample with the antibody-immobilized carrier;

a washing step of washing the antibody-immobilized carrier to which the Aβ related peptide is bound;

an eluting step of dissociating and eluting the Aβ related peptide from the antibody-immobilized carrier by using an acidic solution to obtain a purified solution; and a step of detecting the Aβ related peptide in the purified solution by mass spectrometry.

(7) The method according to the above item (6), wherein the acidic solution is an acidic solution containing a surfactant.

(8) The method according to the above item (6) or (7), wherein the biological sample is a living body-derived sample selected from the group consisting of blood, cerebrospinal fluid, urine, feces, and body secreting fluid.

(9) The method according to the above item (6) or (7), wherein the biological sample is whole blood, plasma or serum.

(10) The method according to any one of the above items (6) to (9), wherein in the mass spectrometry, a matrix-assisted laser desorption/ionization mass spectrometer is used.

(11) A method for measuring an Aβ related peptide in a biological sample, the method comprising:

a first reaction step of bringing a liquid containing a biological sample into contact with a first antibody-immobilized carrier that includes a carrier and the monoclonal antibody according to the above item (1) bound to the carrier, to bind an Aβ related peptide in the biological sample with the first antibody-immobilized carrier;

a first washing step of washing the first antibody-immobilized carrier to which the Aβ related peptide is bound;

a first eluting step of dissociating and eluting the Aβ related peptide from the first antibody-immobilized carrier by using an acidic solution to obtain a first eluate, a neutralizing step of making pH of the eluate neutral by adding a neutral buffer to the first eluate to obtain a first purified solution with neutralized pH;

a second reaction step of bringing the first purified solution into contact with a second antibody-immobilized carrier that includes a carrier and the antibody according to the above item (1) bound to the carrier, to bind the Aβ related peptide in the first purified solution with the second antibody-immobilized carrier;

a second washing step of washing the second antibody-immobilized carrier to which the Aβ related peptide is bound;

a second eluting step of dissociating and eluting the Aβ related peptide from the second antibody-immobilized carrier by using an acidic solution to obtain a second purified solution; and a step of detecting the Aβ related peptide in the second purified solution by mass spectrometry.

(12) The method according to the above item (11), wherein a liquid amount of the first purified solution subjected to the second reaction step is smaller than a liquid amount of the liquid containing a biological sample subjected to the first reaction step.

(13) The method according to the above item (11) or (12), wherein an amount of the second antibody-immobilizing carrier in the second reaction step is smaller than an amount of the first antibody-immobilizing carrier in the first reaction step.

(14) The method according to any one of the above items (11) to (13), wherein in the first eluting step, the acidic solution is an acidic solution containing a surfactant.

(15) The method according to any one of the above items (11) to (14), wherein in the second eluting step, the acidic solution is an acidic solution containing an organic solvent.

(16) The method according to any one of the above items (11) to (15), wherein the biological sample is a living body-derived sample selected from the group consisting of blood, cerebrospinal fluid, urine, feces, and body secreting fluid.

(17) The method according to any one of the above items (11) to (15), wherein the biological sample is whole blood, plasma or serum.

(18) The method according to any one of the above items (11) to (17), wherein in the mass spectrometry, a matrix-assisted laser desorption/ionization mass spectrometer is used.

(19) A method for measuring an Aβ related peptide in a biological sample, the method comprising:

a reaction step of bringing a liquid containing a biological sample into contact with the monoclonal antibody according to the above item (1), to bind an Aβ related peptide in the biological sample with the monoclonal antibody;

a step of detecting the Aβ related peptide binding with the monoclonal antibody by a method selected from the group consisting of a sandwich immunoassay method, a direct ELISA, an indirect ELISA, a competitive ELISA, a western blotting, an immunohistochemistry, a flow cytometry, an immunoprecipitation, an affinity chromatography, and an immunocytochemistry.

(20) A monoclonal antibody that recognizes Aβ3-8 peptide (SEQ ID NO: 1).

(21) A monoclonal antibody that recognizes Aβ3-8 peptide, and is produced by a hybridoma deposited under the accession number NITE BP-02998 at the NITE Patent Microorganisms Depositary of the National Institute of Technology and Evaluation.

The invention claimed is:

1. A monoclonal antibody that recognizes an Aβ related peptide, and is produced by a hybridoma deposited under the accession number NITE BP-02998 at the NITE Patent Microorganisms Depositary of the National Institute of Technology and Evaluation, wherein "Aβ" stands for amyloid beta.

2. An antibody-immobilized carrier that comprises a carrier and the monoclonal antibody according to claim 1 bound to the carrier.

3. A kit for measuring an Aβ related peptide, comprising the antibody-immobilized carrier according to claim 2.

4. A hybridoma deposited under the accession number NITE BP-02998 at the NITE Patent Microorganisms Depositary of the National Institute of Technology and Evaluation.

5. The hybridoma according to claim 4, having an ability to produce a monoclonal antibody that recognizes an Aβ related peptide.

6. A method for measuring an Aβ related peptide in a biological sample, the method comprising:

a reaction step of bringing a liquid containing a biological sample into contact with an antibody-immobilized carrier that comprises a carrier and the monoclonal antibody according to claim 1 bound to the carrier, to bind an Aβ related peptide in the biological sample with the antibody-immobilized carrier;

a washing step of washing the antibody-immobilized carrier to which the Aβ related peptide is bound;

an eluting step of dissociating and eluting the Aβ related peptide from the antibody-immobilized carrier by using an acidic solution to obtain a purified solution; and a step of detecting the Aβ related peptide in the purified solution by mass spectrometry.

7. The method according to claim 6, wherein the biological sample is whole blood, plasma or serum.

8. A method for measuring an Aβ related peptide in a biological sample, the method comprising:

a first reaction step of bringing a liquid containing a biological sample into contact with a first antibody-immobilized carrier that comprises a carrier and the monoclonal antibody according to claim 1 bound to the carrier, to bind an Aβ related peptide in the biological sample with the first antibody-immobilized carrier;

a first washing step of washing the first antibody-immobilized carrier to which the Aβ related peptide is bound;

a first eluting step of dissociating and eluting the Aβ related peptide from the first antibody-immobilized carrier by using an acidic solution to obtain a first eluate, a neutralizing step of making pH of the eluate neutral by adding a neutral buffer to the first eluate to obtain a first purified solution with neutralized pH;

a second reaction step of bringing the first purified solution into contact with a second antibody-immobilized carrier that includes a carrier and the antibody according to claim 1 bound to the carrier, to bind the Aβ related peptide in the first purified solution with the second antibody-immobilized carrier;

a second washing step of washing the second antibody-immobilized carrier to which the Aβ related peptide is bound;

a second eluting step of dissociating and eluting the Aβ related peptide from the second antibody-immobilized carrier by using an acidic solution to obtain a second purified solution; and a step of detecting the Aβ related peptide in the second purified solution by mass spectrometry.

9. The method according to claim 8, wherein in the first eluting step, the acidic solution is an acidic solution containing a surfactant.

10. The method according to claim 8, wherein in the second eluting step, the acidic solution is an acidic solution containing an organic solvent.

11. The method according to claim 8, wherein the biological sample is whole blood, plasma or serum.

12. A method for measuring an Aβ related peptide in a biological sample, the method comprising:

a reaction step of bringing a liquid containing a biological sample into contact with the monoclonal antibody according to claim 1, to bind an Aβ related peptide in the biological sample with the monoclonal antibody;

a step of detecting the Aβ related peptide binding with the monoclonal antibody by a method selected from the group consisting of a sandwich immunoassay method, a direct ELISA, an indirect ELISA, a competitive ELISA, a western blotting, an immunohistochemistry, a flow cytometry, an immunoprecipitation, an affinity chromatography, and an immunocytochemistry.

13. The monoclonal antibody according to claim 1, that recognizes Aβ3-8 peptide (SEQ ID NO: 1).

14. The hybridoma according to claim 5, wherein the Aβ related peptide comprises includes Aβ3-8 peptide (SEQ ID NO: 1).

* * * * *

SEQUENCE LISTING

```
<160> NUMBER OF SEQ ID NOS: 10

<210> SEQ ID NO 1
<211> LENGTH: 6
<212> TYPE: PRT
<213> ORGANISM: Homo sapiens

<400> SEQUENCE: 1

Glu Phe Arg His Asp Ser
1               5

<210> SEQ ID NO 2
<211> LENGTH: 37
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly
        35

<210> SEQ ID NO 3
```

-continued

```
<211> LENGTH: 38
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 4
<211> LENGTH: 39
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35

<210> SEQ ID NO 5
<211> LENGTH: 40
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 41
<212> TYPE: PRT
<213> ORGANISM: Homo sapiens

<400> SEQUENCE: 7

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30
```

```
Ala Ile Ile Gly Leu Met Val Gly Gly
        35                  40

<210> SEQ ID NO 8
<211> LENGTH: 42
<212> TYPE: PRT
<213> ORGANISM: Homo sapiens

<400> SEQUENCE: 8

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val
        35                  40

<210> SEQ ID NO 9
<211> LENGTH: 43
<212> TYPE: PRT
<213> ORGANISM: Homo sapiens

<400> SEQUENCE: 9

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val
        35                  40

<210> SEQ ID NO 10
<211> LENGTH: 17
<212> TYPE: PRT
<213> ORGANISM: Homo sapiens

<400> SEQUENCE: 10

Asp Ala Glu Phe Arg His Asp Ser Gly Tyr Glu Val His His Gln Lys
1               5                   10                  15

Cys
```